(12) United States Patent
Kim et al.

(10) Patent No.: US 12,111,318 B2
(45) Date of Patent: Oct. 8, 2024

(54) METHOD FOR TREATING CANCER BASED ON EXPRESSION LEVELS OF TRANSLATIONALLY CONTROLLED TUMOR PROTEIN (TCTP)

(71) Applicant: KOREA UNIVERSITY RESEARCH AND BUSINESS FOUNDATION, Seoul (KR)

(72) Inventors: Tae Woo Kim, Seoul (KR); Hyo Jung Lee, Gyeonggi-do (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 54 days.

(21) Appl. No.: 17/528,578

(22) Filed: Nov. 17, 2021

(65) Prior Publication Data

US 2022/0155303 A1 May 19, 2022

(30) Foreign Application Priority Data

Nov. 17, 2020 (KR) ........................ 10-2020-0154101

(51) Int. Cl.
*G01N 33/574* (2006.01)
*G01N 33/50* (2006.01)

(52) U.S. Cl.
CPC ..... *G01N 33/5748* (2013.01); *G01N 33/5011* (2013.01); *G01N 2333/521* (2013.01); *G01N 2333/71* (2013.01); *G01N 2333/91215* (2013.01)

(58) Field of Classification Search
CPC ........... G01N 33/5748; G01N 33/5011; G01N 2333/521; G01N 2333/71; G01N 2333/91215
See application file for complete search history.

(56) References Cited

U.S. PATENT DOCUMENTS

2020/0157633 A1  5/2020  Regev et al.

FOREIGN PATENT DOCUMENTS

| WO | WO-2016/100975 A8 | 6/2017 |
| WO | WO-2018/183821 A1 | 10/2018 |
| WO | WO-2018/183921 A1 | 10/2018 |

OTHER PUBLICATIONS

Lee, HJ et al. (2022). Nature Communications, vol. 13, Article No. 2127.*
Chen C, et al. (Apr. 2015) J Mol Histol. 46(2):145-56. (doi: 10.1007/s10735-014-9607-y. Epub Jan. 7, 2015).*
Jung J, et al. (Mar. 7, 2014) BMC Cancer. 14:165. (doi: 10.1186/1471-2407-14-165).*
Jung J, et al. (Mar. 19, 2019) Cancers (Basel). 11(3):386. (doi: 10.3390/cancers11030386).*
Bommer U-A, et al. (2017) Cell Communication and Signaling. 15(9). 15 pages. (doi. 10.1186/s12964-017-0164-3).*
Xiang W, et al. (2018) OncoTargets and Therapy. 11:7301-7314. (http://dx.doi.org/10.2147/OTT.S146228).*
Bae Sy, et al. (Jan. 27, 2015) Scientific Reports. 5: 8061 (9 pages). (doi: 10.1038/srep08061).*
Yang, Y. "Cancer immunotherapy: harnessing the immune system to battle cancer", The Journal of Clinical Investigation, vol. 125, No. 9, Sep. 2015, pp. 3335-3337.
Sharma, P., et al.; "Primary, adaptive, and acquired resistance to cancer immunotherapy", Cell 168, Feb. 9, 2017, pp. 707-723.
Office Action from corresponding Korean Patent Application No. 10-2020-0154101, dated Sep. 20, 2022.
Du, J., et al.; "Aberrant expression of translationally controlled tumor protein (TCTP) can lead to radioactive susceptibility and chemosensitivity in lung cancer cells", Oncotarget, 2017, vol. 8, (No. 60), pp. 101922-101935.
Office Action from Korean patent application No. 10-2020-0154101 dated Dec. 19, 2023.
Fischer et al. "High TCTP expression as prognostic factor in different cancer types" World Acad Sci J, 3(1): 1-12 (Nov. 9, 2020).
Acunzo et al. "TCTP as therapeutic target in cancers" Cancer Treat Rev, 40(6): 760-769 (Mar. 2, 2014).
Notice of Allowance from corresponding Korean Patent Application No. 10-2020-0154101 issued on Jul. 12, 2024.

* cited by examiner

*Primary Examiner* — Robert S Landsman
(74) *Attorney, Agent, or Firm* — Harness, Dickey & Pierce, P.L.C.

(57) ABSTRACT

Disclosed herein are a method and a biomarker for predicting efficacy and prognosis of or resistance to an immunotherapy. The use of the biomarkers (TCTP, EGFR, AKT, MCL1, and/or CXCL10) of the present disclosure allows the prediction of resistance to or prognosis of a cancer immunotherapeutic agent and the selection of a therapy guaranteeing therapeutic benefit, thereby finding advantageous applications in treating cancers or tumors resistant to cancer immunotherapeutic agents.

5 Claims, 43 Drawing Sheets

Specification includes a Sequence Listing.

SEQUENCE LISTING

<160> NUMBER OF SEQ ID NOS: 20

<210> SEQ ID NO 1
<211> LENGTH: 41
<212> TYPE: DNA
<213> ORGANISM: Artificial Sequence
<220> FEATURE:
<223> OTHER INFORMATION: TCTP S46D forward

<400> SEQUENCE: 1
ggtaacattg atgacgacct cattggtgga aatgcctccg c          41

<210> SEQ ID NO 2
<211> LENGTH: 41
<212> TYPE: DNA
<213> ORGANISM: Artificial Sequence
<220> FEATURE:
<223> OTHER INFORMATION: TCTP S46D reverse

<400> SEQUENCE: 2
gcggaggcat ttccaccaat gaggtcgtca tcaatgttac c          41

<210> SEQ ID NO 3
<211> LENGTH: 41
<212> TYPE: DNA
<213> ORGANISM: Artificial Sequence
<220> FEATURE:
<223> OTHER INFORMATION: TCTP S46A forward

<400> SEQUENCE: 3
cgagggcgaa ggtaccgaag caacagtaat cactggtgtc g          41

<210> SEQ ID NO 4
<211> LENGTH: 41
<212> TYPE: DNA
<213> ORGANISM: Artificial Sequence
<220> FEATURE:
<223> OTHER INFORMATION: TCTP S46A reverse

<400> SEQUENCE: 4
cgacaccagt gattactgtt gcttcggtac cttcgccctc g          41

<210> SEQ ID NO 5
<211> LENGTH: 20
<212> TYPE: DNA
<213> ORGANISM: Artificial Sequence
<220> FEATURE:
<223> OTHER INFORMATION: TPT1 forward

<400> SEQUENCE: 5
atgacgagct gttctccgac                                  20

<210> SEQ ID NO 6

```
<211> LENGTH: 20
<212> TYPE: DNA
<213> ORGANISM: Artificial Sequence
<220> FEATURE:
<223> OTHER INFORMATION: TPT1 reverse

<400> SEQUENCE: 6
aacaccggtg actactgtgc                                               20

<210> SEQ ID NO 7
<211> LENGTH: 19
<212> TYPE: RNA
<213> ORGANISM: Artificial Sequence
<220> FEATURE:
<223> OTHER INFORMATION: GFP sense

<400> SEQUENCE: 7
gcaucaaggu gaacuucaa                                                19

<210> SEQ ID NO 8
<211> LENGTH: 19
<212> TYPE: RNA
<213> ORGANISM: Artificial Sequence
<220> FEATURE:
<223> OTHER INFORMATION: GFP antisense

<400> SEQUENCE: 8
uugaaguuca ccuugaugc                                                19

<210> SEQ ID NO 9
<211> LENGTH: 19
<212> TYPE: RNA
<213> ORGANISM: Artificial Sequence
<220> FEATURE:
<223> OTHER INFORMATION: mouse TPT1 No.1 sense

<400> SEQUENCE: 9
gaaaucacuc aaaggcaaa                                                19

<210> SEQ ID NO 10
<211> LENGTH: 19
<212> TYPE: RNA
<213> ORGANISM: Artificial Sequence
<220> FEATURE:
<223> OTHER INFORMATION: mouse TPT1 No.1 antisense

<400> SEQUENCE: 10
uuugccuuug agugauuuc                                                19

<210> SEQ ID NO 11
<211> LENGTH: 19
<212> TYPE: RNA
<213> ORGANISM: Artificial Sequence
<220> FEATURE:
<223> OTHER INFORMATION: mouse TPT1 No.2 sense

<400> SEQUENCE: 11
cuguucuccg acaucuaca                                                19

<210> SEQ ID NO 12
<211> LENGTH: 19
<212> TYPE: RNA
<213> ORGANISM: Artificial Sequence
<220> FEATURE:
<223> OTHER INFORMATION: mouse TPT1 No.2 antisense

<400> SEQUENCE: 12
```

```
uguagauguc ggagaacag                                                    19

<210> SEQ ID NO 13
<211> LENGTH: 21
<212> TYPE: DNA
<213> ORGANISM: Artificial Sequence
<220> FEATURE:
<223> OTHER INFORMATION: mouse TPT1 No.3 sense

<400> SEQUENCE: 13
agcacauccu ugcuaauuut t                                                 21

<210> SEQ ID NO 14
<211> LENGTH: 21
<212> TYPE: DNA
<213> ORGANISM: Artificial Sequence
<220> FEATURE:
<223> OTHER INFORMATION: mouse TPT1 No.3 antisense

<400> SEQUENCE: 14
aaauuagcaa ggaugugcut a                                                 21

<210> SEQ ID NO 15
<211> LENGTH: 19
<212> TYPE: RNA
<213> ORGANISM: Artificial Sequence
<220> FEATURE:
<223> OTHER INFORMATION: human TPT1 sense

<400> SEQUENCE: 15
gcaugguugc ucuauugga                                                    19

<210> SEQ ID NO 16
<211> LENGTH: 19
<212> TYPE: RNA
<213> ORGANISM: Artificial Sequence
<220> FEATURE:
<223> OTHER INFORMATION: human TPT1 antisense

<400> SEQUENCE: 16
uccaauagag caaccaugc                                                    19

<210> SEQ ID NO 17
<211> LENGTH: 21
<212> TYPE: RNA
<213> ORGANISM: Artificial Sequence
<220> FEATURE:
<223> OTHER INFORMATION: human EGFR sense

<400> SEQUENCE: 17
aggaauuaag agaagcaaca u                                                 21

<210> SEQ ID NO 18
<211> LENGTH: 21
<212> TYPE: RNA
<213> ORGANISM: Artificial Sequence
<220> FEATURE:
<223> OTHER INFORMATION: human EGFR antisense

<400> SEQUENCE: 18
auguugcuuc ucuuaauucc u                                                 21

<210> SEQ ID NO 19
<211> LENGTH: 25
<212> TYPE: RNA
```

```
<213> ORGANISM: Artificial Sequence
<220> FEATURE:
<223> OTHER INFORMATION: mouse MCL-1 sense

<400> SEQUENCE: 19
gggcaggauu gugacucuua uuucu                                      25

<210> SEQ ID NO 20
<211> LENGTH: 25
<212> TYPE: RNA
<213> ORGANISM: Artificial Sequence
<220> FEATURE:
<223> OTHER INFORMATION: mouse MCL-1 antisense

<400> SEQUENCE: 20
agaaauaaga gucacaaucc ugccc                                      25
```

METHOD FOR TREATING CANCER BASED ON EXPRESSION LEVELS OF TRANSLATIONALLY CONTROLLED TUMOR PROTEIN (TCTP)

CROSS REFERENCE TO RELATED APPLICATIONS

This application claims the benefit of the Korean Patent Application No. 10-2020-0154101 filed on Nov. 17, 2020, which is hereby incorporated by reference as if fully set forth herein.

FIELD

The present disclosure relates to a use of TCTP as a biomarker for predicting immunotherapy efficacy or prognosis or resistance to immunotherapy and as a target for enhancing immunotherapy efficacy.

BACKGROUND

A main goal of cancer immunotherapy is to start or restart self-sustaining cycles of anti-cancer immunity having sustained clinical responses. However, most patients exhibit immunotherapy resistance because of their inability to amplify and advance the cycles. In order to surmount resistance to immunotherapy, there is therefore a need for identifying a resistance factor responsible for one or more steps of the cancer immunity cycle and for examining whether resistance to immunotherapy is eliminated through reversal of the resistance factor.

RELATED ART DOCUMENT

Non-Patent Literatures

Yang, Y. Cancer immunotherapy: harnessing the immune system to battle cancer. *The Journal of clinical investigation* 125, 3335-3337 (2015).

Sharma, P., Hu-Lieskovan, S., Wargo, J. A. & Ribas, A. Primary, adaptive, and acquired resistance to cancer immunotherapy. *Cell* 168, 707-723 (2017).

SUMMARY OF THE INVENTION

Leading to the present disclosure, intensive and thorough research was conducted into the provision of information necessary for predicting resistance to and prognosis of immunotherapy and for selecting a suitable therapy for cancer.

1) Therefore, an aspect of the present disclosure is to provide a method for providing information necessary for predicting resistance to immunotherapy for cancer or tumors.
2) Another aspect of the present disclosure is to provide a method for providing information necessary for predicting responsiveness to or prognosis of the administration of a cancer immunotherapeutic agent for cancer or tumors.
3) A further aspect of the present disclosure is to provide a method for providing information for use in selecting a therapy for an individual with cancer.
4) A further another aspect of the present disclosure is to provide a composition for augmenting efficacy of a cancer immunotherapeutic agent in an individual suffering from cancer, the composition comprising (a) a TCTP inhibitor as an active ingredient; and (b) a pharmaceutically acceptable carrier, excipient, or diluent.
5) A still further aspect of the present disclosure is to provide a composition for treating cancer in an individual suffering from cancer, the composition comprising: (a) a TCTP inhibitor and an immunotherapeutic agent as active ingredients; and (b) a pharmaceutically acceptable carrier, excipient, or diluent.
6) Still another aspect of the present disclosure is to provide a kit comprising at least one reagent for determining presence or an expression level of TCTP in a sample isolated from an individual with cancer.

The present disclosure pertains to a biomarker for predicting efficacy or prognosis of an immunotherapy or resistance to an immunotherapy and to a use of TCTP as a target for enhancing efficacy of an immunotherapy.

Specifically, the present disclosure provides a method for providing information necessary for prediction of resistance to a cancer immunotherapeutic agent for cancer or tumor, a method for providing information necessary for predicting responsiveness to or prognosis of the administration of a cancer immunotherapeutic agent for cancer or tumor, a method for providing information for selecting a therapy for an individual suffering from cancer, a composition for augmenting efficacy of an immunotherapeutic agent, a composition for treatment of cancer, and a kit comprising at least one agent for determining presence or an expression level of TCTP in a sample isolated from an individual suffering from cancer.

As used herein, the term "biomarker" refers to an indicator, e.g., predictive, diagnostic, and/or prognostic, which can be detected in a sample. The biomarker may serve as an indicator of a particular subtype of a disease or disorder (e.g., cancer) characterized by certain molecular, pathological, histological, and/or clinical features. In some embodiments, a biomarker is a gene. Biomarkers include, but are not limited to, polynucleotides (e.g., DNA and/or RNA), polynucleotide copy number alterations (e.g., DNA copy numbers), polypeptides, polypeptide and polynucleotide modifications (e.g., posttranslational modifications), carbohydrates, and/or glycolipid-based molecular markers.

The "amount" or "level" of a biomarker associated with an increased clinical benefit to an individual is a detectable level in a biological sample. These can be measured by methods known to one skilled in the art and also disclosed herein. The expression level or amount of biomarker assessed can be used to determine the response to the treatment.

As used herein, the terms "level of expression" or "expression level" generally refer to the amount of a biomarker in a biological sample. "Expression" generally refers to the process by which information (e.g., gene-encoded and/or epigenetic) is converted into the structures present and operating in the cell. Therefore, as used herein, "expression" may refer to transcription into a polynucleotide, translation into a polypeptide, or even polynucleotide and/or polypeptide modifications (e.g., posttranslational modification of a polypeptide). Fragments of the transcribed polynucleotide, the translated polypeptide, or polynucleotide and/or polypeptide modifications (e.g., posttranslational modification of a polypeptide) shall also be regarded as being expressed whether they originate from a transcript generated by alternative splicing or a degraded transcript, or from a post-translational processing of the polypeptide, e.g., by proteolysis. "Expressed genes" include those that are transcribed into a polynucleotide as mRNA and then translated into a polypeptide, and also those that are transcribed into RNA but not translated into a polypeptide (for example, tRNAs and rRNAs).

"Elevated expression", "elevated expression levels", or "elevated levels" refers to an increased expression or increased levels of a biomarker in an individual relative to a control, such as an individual or individuals who are not suffering from the disease or disorder (e.g., cancer) or an internal control (e.g., housekeeping biomarker).

"Reduced expression", "reduced expression levels", or "reduced levels" refers to a decrease expression or decreased levels of a biomarker in an individual relative to a control, such as an individual or individuals who are not suffering from the disease or disorder (e.g., cancer) or an internal control (e.g., housekeeping biomarker). In some embodiments, reduced expression means little or no expression.

The term "housekeeping biomarker", as used herein, refers to a biomarker or group of biomarkers (e.g., polynucleotides and/or polypeptides) which are typically similarly present in all cell types. In some embodiments, the housekeeping biomarker is a "housekeeping gene". A "housekeeping gene" refers herein to a gene or group of genes which encode proteins whose activities are essential for the maintenance of cell function and which are typically similarly present in all cell types.

The term "polynucleotide", when used in singular or plural, generally refers to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide", as used herein, refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically, and/or metabolically modified forms of unmodified polynucleotides, as well as the chemical forms of DNA and RNA characteristic of viruses and cells (including simple and complex cells).

The term "oligonucleotide", as used herein, refers to a relatively short polynucleotide, including, without limitation, single-stranded deoxyribonucleotides, single- or double-stranded ribonucleotides, RNA:DNA hybrids, and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The term "diagnosis" is used herein to refer to the identification or classification of a molecular or pathological state, disease, or condition (e.g., cancer). For example, "diagnosis" may refer to identification of a particular type of cancer. "Diagnosis" may also refer to the classification of a particular subtype of cancer, e.g., by histopathological criteria, or by molecular features (e.g., a subtype characterized by expression of one or a combination of biomarkers (e.g., particular genes or proteins encoded by said genes)).

The term "sample", as used herein, refers to a composition that is obtained or derived from a subject and/or individual of interest that contains a cellular and/or other molecular entity that is to be characterized and/or identified, for example, based on physical, biochemical, chemical and/or physiological characteristics. For example, the phrase "disease sample" and variations thereof refers to any sample obtained from a subject of interest that would be expected or is known to contain the cellular and/or molecular entity that is to be characterized. Samples include, but are not limited to, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, blood-derived cells, urine, cerebrospinal fluid, saliva, sputum, tears, perspiration, mucus, tumor lysates, and tissue culture medium, tissue extracts such as homogenized tissue, tumor tissue, cellular extracts, and combinations thereof, but with no limitations thereto.

By "tissue sample" or "cell sample" is meant herein a collection of similar cells obtained from a tissue of a subject or individual. The source of the tissue or cell sample may be solid tissue as from a fresh, frozen, and/or preserved organ, tissue sample, biopsy, and/or aspirate; blood or any blood constituents such as plasma; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like.

A "reference sample", "reference cell", "reference tissue", "control sample", "control cell", or "control tissue", as used herein, refers to a sample, cell, tissue, standard, or level that is used for comparison purposes. In one embodiment, a reference sample, reference cell, reference tissue, control sample, control cell, or control tissue is obtained from a healthy and/or non-diseased part of the body (e.g., tissue or cells) of the same subject or individual. For example, healthy and/or non-diseased cells or tissue adjacent to the diseased cells or tissue (e.g., cells or tissue adjacent to a tumor). In another embodiment, a reference sample is obtained from an untreated tissue and/or cell of the body of the same subject or individual. In yet another embodiment, a reference sample, reference cell, reference tissue, control sample, control cell, or control tissue is obtained from a healthy and/or non-diseased part of the body (e.g., tissues or cells) of an individual who is not the subject or individual. In even another embodiment, a reference sample, reference cell, reference tissue, control sample, control cell, or control tissue is obtained from an untreated tissue and/or cell of the body of an individual who is not the subject or individual.

In one embodiment of the present disclosure, a reference sample (specimen), reference cell, reference tissue, control sample, control cell, or control tissue is obtained from an individual, tissue, or cell that is not resistant to a cancer immunotherapy. In an embodiment of the present disclosure, the individual or cell that has no resistance to the cancer immunotherapy includes, for example, CT26 P0, A375 P0, TC-1 LP0, etc., but with no limitations thereto.

An "effective response" of a patient or a patient's "responsiveness" to treatment with a medicament and similar wording refers to the clinical or therapeutic benefit imparted to a patient at risk for, or suffering from, a disease or disorder, such as cancer.

In one embodiment, such benefit includes any one or more of: extending survival (including overall survival and progression free survival); resulting in an objective response (including a complete response or a partial response); or improving signs or symptoms of cancer. In one embodiment, the biomarker (e.g., TCTP expression, for example, as determined by real-time qPCR) is used to identify the patient who is predicted to have an increase likelihood of being resistant to treatment with a medicament (e.g., anti-PD-L1 antibody), relative to a patient who does not express the biomarker. In one embodiment, the biomarker (e.g., TCTP expression, for example, as determined by real-time qPCR) is used to identify the patient who is predicted to have an increase likelihood of being resistant to treatment with a medicament (e.g., anti-PD-L1 antibody), relative to a patient who expresses the biomarker at a lower level.

An "individual" or "subject" is a mammal. The mammals may include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

According to an aspect thereof, the present disclosure provides a method for providing information necessary for prediction of resistance to an immunotherapeutic agent for cancer or tumor, the method comprising the steps of:
  (a) measuring presence or expression of TCTP (translationally controlled tumor protein) at a protein or gene level in a sample isolated from an individual; and
  (b) providing information necessary for prediction of resistance to an immunotherapeutic agent for cancer or tumor.

As used herein, the term "TCTP" (translationally controlled tumor protein) is a protein that is encoded by the TPT1 gene in humans. The TPT1 gene is mapped to 13q12-q1413 in the chromosome 13. The TPT1 gene contains five introns and six exons. This gene is highly conserved in mammals and is known to have relevance to cell growth, immunity, and cancer development. Herein, TCTP and TPT1 are interchangeably used.

The term "EGFR" (epidermal growth factor receptor; ErbB-1; HER1 in humans), as used herein, refers to a transmembrane protein that is a receptor for members of the epidermal growth factor family (EGF family) of extracellular protein ligands. The epidermal growth factor receptor is a member of the ErbB family of receptors, a subfamily of four closely related receptor tyrosine kinases (EGFR (ErbB-1), HER2/neu (ErbB-2), Her 3 (ErbB-3), and Her 4 (ErbB-4)). In many cancer types, mutations affecting EGFR expression or activity are known to result in cancer.

RAC-alpha serine/threonine-protein kinase is an enzyme that in humans is encoded by the AKT1 gene. This enzyme belongs to the AKT subfamily of serine/threonine kinases that contain SH2 (Src homology 2-like) protein domains.

Induced myeloid leukemia cell differentiation protein Mcl-1 is a protein that in humans is encoded by the MCL1 gene. The MCL-1 gene belongs to the Bcl-2 family. Alternative splicing occurs at this locus, producing two transcript variants encoding distinct isoforms. The longer gene product (isoform 1) enhances cell survival by inhibiting apoptosis while the alternatively spliced shorter gene product (isoform 2) is known to induce cell death by promoting apoptosis.

CXCL10 (C-X-C motif chemokine ligand 10), also known as IP-10 (interferon gamma-induced protein 10) or small-inducible cytokine B10, is an 8.7 kDa protein that in humans is encoded by the CXCL10 gene. CXCL10 is a small cytokine belonging to the CXC chemokine family.

In an embodiment of the present disclosure, a higher measurement of the presence or expression of TCTP (translationally controlled tumor protein) at a protein or gene level in step (a) than that in a reference sample indicates the likelihood that the cancer or tumor is more resistant to the cancer immunotherapeutic agent.

In an embodiment of the present disclosure, step (a) may further comprise measuring presence or expression of at least one selected from the group consisting of EGFR, AKT, MCL1, NANOG, and CXCL10 at a gene or protein level.

In an embodiment of the present disclosure, a higher measurement of the presence or expression of one selected from the group consisting of EGFR, AKT, MCL1, NANOG, and a combination thereof at a gene or protein level than that in a reference sample indicates the likelihood that the cancer or tumor is more resistant to the cancer immunotherapeutic agent.

In an embodiment of the present disclosure, a lower measurement of the presence or expression of CXCL10 at a gene or protein level than that in a reference sample indicates the likelihood that the cancer or tumor is more resistant to the immunotherapeutic agent.

In an embodiment of the present disclosure, the biomarker of the present disclosure is selected from the group consisting of TCTP, EGFR, AKT, MCL1, NANOG, and CXCL10.

In an embodiment of the present disclosure, the biomarker is absence from the sample when it comprises 0% of the sample. In an embodiment of the present disclosure, the biomarker is present in the same when it comprises more than 0% of the sample. In an embodiment of the present disclosure, the biomarker is present in at least 1%, 2%, 3%, 4%, 5%, or 10% of the sample.

In an embodiment of the present disclosure, the biomarker is detected in the sample using a method selected from the group consisting of FACS, Western blot, ELISA, immunoprecipitation, immunohistochemistry, immunofluorescence, radioimmunoassay, dot blotting, immunodetection methods, HPLC, surface plasmon resonance, optical spectroscopy, mass spectrometry, qPCR, RT-qPCR, multiplex qPCR or RT-qPCR, RNA-seq, microarray analysis, SAGE, Mass ARRAY technique, and FISH, and a combination thereof.

In an embodiment of the present disclosure, the biomarker is detected in the sample by protein detection. In an embodiment of the present disclosure, the protein detection is carried out by immunohistochemistry (IHC) or Western blot. In an embodiment of the present disclosure, the TCTP biomarker is detected using an anti-TCTP antibody.

In an embodiment of the present disclosure, the biomarker is detected in the sample by nucleic acid replication. In some exemplary embodiments, the nucleic acid replication is carried out by qPCR, rtPCR, RNA-seq, multiplex qPCR or RT-qPCR, microarray analysis, SAGE, MassARRAY technique, or FISH.

In an embodiment of the present disclosure, the biomarker is detected on tumor cells, tumor infiltrating immune cells, stromal cells, and a combination thereof by nucleic acid expression such as qPCR analysis.

In an embodiment of the present disclosure, the cancer is selected from non-small cell lung cancer, small cell lung cancer, renal cell cancer, colorectal cancer, ovarian cancer, breast cancer, pancreatic cancer, gastric carcinoma, bladder cancer, esophageal cancer, mesothelioma, melanoma, head and neck cancer, thyroid cancer, sarcoma, prostate cancer, glioblastoma, cervical cancer, thymic carcinoma, leukemia, lymphomas, myelomas, Merkle cell cancer, and hematologic malignancies.

According to another aspect thereof, the present disclosure provides a method for providing information necessary for predicting responsiveness to or prognosis of the administration of a cancer immunotherapeutic agent, the method comprising the steps of:
(a) measuring presence or expression of TCTP (translationally controlled tumor protein) at a protein or gene level in a sample isolated from an individual; and
(b) providing information necessary for predicting responsiveness to or prognosis of the administration of a cancer immunotherapeutic agent, in which an individual would be highly likely to be responsive to or have a good prognosis for the administration of the cancer immunotherapeutic agent.

In an embodiment of the present disclosure, a higher measurement of the presence or expression of TCTP (translationally controlled tumor protein) at a protein or gene level in step (a) than that in a reference sample indicates the likelihood that the individual is lower responsive to or has a poorer prognosis for the cancer immunotherapeutic agent. In an embodiment of the present disclosure, step (a) may further comprise measuring presence or expression of at least one selected from the group consisting of EGFR, AKT, MCL1, NANOG, and CXCL10 at a gene or protein level.

In an embodiment of the present disclosure, a higher measurement of the presence or expression of one selected from the group consisting of EGFR, AKT, MCL1, NANOG, and a combination thereof at a gene or protein level than that in a reference sample indicates the likelihood that the individual is less responsive to the cancer immunotherapeutic agent.

In an embodiment of the present disclosure, a lower measurement of the presence or expression of CXCL10 at a gene or protein level than that in a reference sample indicates the likelihood that the individual is less responsive to the immunotherapeutic agent.

The method for providing information necessary for predicting responsiveness to or prognosis of the administration of a cancer immunotherapeutic agent according to an aspect of the present disclosure has steps and configuration in common with the aforementioned method for providing information necessary for predicting resistance to an immunotherapeutic agent for cancer or tumor, so that the same description is applied to the overlapping range.

According to another aspect thereof, the present disclosure provides a method for providing information for use in selecting a therapy for an individual suffering from cancer, the method comprising the steps of:
(a) measuring presence or an expression level of TCTP (translationally controlled tumor protein) in a sample isolated from an individual; and
(b) providing information for use in selecting a therapy for the individual, in which the individual is highly likely to exhibit benefit from a therapy using a TCTP protein or gene-targeting inhibitor.

In an embodiment of the present disclosure, a higher measurement of the presence or expression level of TCTP (translationally controlled tumor protein) in step (a) than that in a reference sample indicates the likelihood that the selection of a therapy using a TCTP protein or gene-targeting inhibitor imparts high therapeutic benefit.

In an embodiment of the present disclosure, step (a) may further comprise measuring presence or expression of at least one selected from the group consisting of EGFR, AKT, MCL1, NANOG, and CXCL10 at a gene or protein level.

In an embodiment of the present disclosure, a higher measurement of the presence or expression of one selected from the group consisting of EGFR, AKT, MCL1, and a combination thereof at a gene or protein level than that in a reference sample indicates the likelihood that the selection of a therapy using a TCTP protein or gene-targeting inhibitor is more likely to impart high therapeutic benefit.

In an embodiment of the present disclosure, a lower measurement of the presence or expression of CXCL10 at a gene or protein level than that in a reference sample indicates the likelihood that the selection of a therapy using a TCTP protein or gene-targeting inhibitor is more likely to impart high therapeutic benefit.

In an embodiment of the present disclosure, a higher measurement of the presence or expression of one selected from the group consisting of EGFR, AKT, MCL-1, and NANOG at a protein or gene level than that in a reference sample or
a lower measurement of the presence or expression of CXCL10 at a protein or gene level than that in a reference sample indicates that a therapy using i) an inhibitor targeting one or more selected from EGFR, AKT, MCL-1, and NANOG at a protein or gene level, ii) a CXCL10 activator at a protein or gene level, or iii) a combination thereof is more likely to impart high therapeutic benefit. This therapy may be used in combination with the TCTP protein or gene-targeting inhibitor.

The method for providing information for use in selecting a therapy for an individual with cancer according to an aspect of the present disclosure has steps and configuration in common with the aforementioned method for providing information necessary for predicting resistance to an immunotherapeutic agent for cancer or tumor, so that the same description is applied to the overlapping range.

As used herein, the terms "inhibitor" targeting any protein or gene (e.g., EGFR protein or gene-targeting inhibitor) and "inhibitor" against any protein or gene (e.g., EGFR inhibitor) are interchangeably used and mean a substance inhibiting the expression or activity of the corresponding matter at a protein or gene level irrespective of types thereof.

Examples of the "inhibitor" targeting any protein or gene or the "inhibitor" against any protein or gene may include an antibody or an antigen-binding fragment thereof, or an antibody-drug conjugate, each binding specifically to the corresponding protein; a compound downregulating the expression or activity of the corresponding protein or gene; a peptide binding specifically to the corresponding protein or downregulating the expression or activity of the corresponding protein or gene; a fusion protein binding specifically to the corresponding protein or downregulating the expression or activity of the corresponding protein or gene; an aptamer binding specifically to the corresponding protein; and an siRNA, an shRNA, an miRNA, a ribozyme, and an antisense oligonucleotide complementarily binding to the corresponding gene, but are not limited thereto.

According to another aspect thereof, the present disclosure provides a pharmaceutical composition for augmenting efficacy of a cancer immunotherapeutic agent in an individual suffering from cancer, the composition comprising: (a) an TCTP inhibitor as an active ingredient; and (b) a pharmaceutically acceptable carrier, excipient, or diluent, wherein a sample isolated from the individual is measured to exhibit higher presence probability or a higher expression level of TCTP compared to a reference sample isolated from an individual suffering from no cancer.

In an embodiment of the present disclosure, the cancer immunotherapeutic agent is an immune checkpoint blocker or an adoptive cell therapeutic agent.

In an embodiment of the present disclosure, the immune checkpoint blocker is an anti-PD-1 agent, an anti-PD-L1 agent, or a combination thereof.

In an embodiment of the present disclosure, the TCTP inhibitor may be an antibody or an antigen-binding fragment thereof, an antibody-drug conjugate, a compound, a peptide, a fusion protein, or an aptamer, which all bind specifically to TCTP.

In an embodiment of the present disclosure, the TCTP inhibitor may be an siRNA, an shRNA, an miRNA, a ribozyme, or an antisense oligonucleotide, which all bind complementarily to a TCTP gene.

In an embodiment of the present disclosure, the siRNA binding complementarily to a TCTP gene includes any one of the sequences of SEQ ID NOS: 9 to 14, but with no limitations thereto.

In an embodiment of the present disclosure, the TCTP inhibitor is at least one drug selected from the group consisting of dihydroartemisinin (DHA), rapamycin, sertraline, and thioridazine, but with no limitations thereto.

In an embodiment of the present disclosure, the cancer is selected from non-small cell lung cancer, small cell lung cancer, renal cell cancer, colorectal cancer, ovarian cancer, breast cancer, pancreatic cancer, gastric carcinoma, bladder cancer, esophageal cancer, mesothelioma, melanoma, head and neck cancer, thyroid cancer, sarcoma, prostate cancer, glioblastoma, cervical cancer, thymic carcinoma, leukemia, lymphomas, myelomas, Merkle cell cancer, and hematologic malignancies, but with no limitations thereto.

As demonstrated in the following Examples, the TCTP inhibitor makes tumor or cancer cells decrease in resistance to and increase in susceptibility to a cancer immunotherapeutic agent such as PD-L1 agent, ACT, etc., thereby finding advantageous application in augmenting efficacy of immunotherapeutic agents.

According to another aspect thereof, the present disclosure provides a pharmaceutical composition for treatment of cancer in an individual suffering from cancer, the composition comprising: (a) a TCTP inhibitor and a cancer immunotherapeutic agent as active ingredients; and (b) a pharmaceutically acceptable carrier, excipient, or diluent, wherein a sample isolated from the individual is measured to exhibit higher presence probability or a higher expression level of TCTP compared to a reference sample isolated from an individual suffering from no cancer.

The pharmaceutical composition for treatment of cancer according to an aspect of the present disclosure has steps and configuration in common with the aforementioned pharmaceutical composition for augmenting efficacy of a cancer immunotherapeutic agent, so that the same description is applied to the overlapping range.

Because the TCTP inhibitor of the present disclosure is in synergy with a cancer immunotherapeutic agent in addition to reducing resistance to the cancer immunotherapeutic agent such as PD-L1 agent, ACT, etc., a combination agent including the TCTP inhibitor and the cancer immunotherapeutic agent can be advantageously used as a cancer therapy with high efficacy.

According to another aspect thereof, the present disclosure provides a kit comprising at least one agent for determining presence or expression of TCTP at a protein or gene level in a sample isolated from an individual with cancer.

In an embodiment of the present disclosure, the kit may further comprise an agent for determining presence or an expression level of at least one gene selected from the group consisting of EGFR, AKT, MCL1, NANOG, and CXCL10.

In an embodiment of the present disclosure, the gene selected from the group consisting of TCTP, EGFR, AKT, MCL1, and CXCL10 is detected by nucleic acid replication in the sample.

In an embodiment of the present disclosure, a higher measurement of presence or expression of TCTP compared to that in a reference sample indicates that the cancer in the individual is more likely to be resistant to the cancer immunotherapeutic agent while a measurement which is the same as or lower than that in a reference sample indicates that the cancer in the individual is less likely to be resistant to the cancer immunotherapeutic agent.

In an embodiment of the present disclosure, the method or kit by which the presence or expression level of a biomarker (TCTP, EGFR, AKT, MCL1, and/or CXCL10) may be used to provide information for maintaining, adjusting, or stopping the treatment of the individual with the cancer immunotherapeutic agent.

According to an embodiment thereof, the present invention provides a method for providing information about a treatment response of an individual to an immunotherapy, the method comprising the steps of: (a) determining presence or an expression level of a biomarker (TCTP, EGFR, AKT, MCL1, and CXCL10) in a sample isolated from an individual suffering from cancer at a time point during or after administration of a cancer immunotherapeutic agent to the individual; (b) comparing the presence or expression level with that of the biomarker (e.g., TCTP) in a sample isolated from the individual at a time point before administration of the cancer immunotherapeutic agent for the biomarker (e.g., TCTP); and (c1) providing information that the individual is more likely to exhibit low responsiveness to or high resistance to the cancer immunotherapeutic agent when the expression level of the biomarker (e.g., TCTP) is increased, or (c2) providing information that the individual is likely to exhibit high or unchanged responsiveness or low resistance to the cancer immunotherapeutic agent when the expression level of the biomarker (e.g., TCTP) is the same or reduced.

Therefore, when there is no resistance to the cancer immunotherapeutic agent or the responsiveness to the cancer immunotherapeutic agent is maintained or increased on the basis of the result from monitoring expression levels of the biomarkers (TCTP, EGFR, AKT, MCL1, and/or CXCL10) before and after administration of the cancer therapeutic agent, the treatment with the cancer immunotherapeutic agent can be maintained or augmented.

In contrast, when there is resistance to the cancer immunotherapeutic agent or the responsiveness to the cancer immunotherapeutic agent is decreased on the basis of the result from monitoring expression levels of the biomarkers (TCTP, EGFR, AKT, MCL1, and/or CXCL10) before and after administration of the cancer therapeutic agent, the treatment with the cancer immunotherapeutic agent can be stopped.

The measurement of expression levels of the biomarkers (TCTP, EGFR, AKT, MCL1, and/or CXCL10) may be performed at least two, three, four, or five times at different points of time, and the use of the cancer immunotherapeutic agent may be maintained, stopped, or restarted depending on changes in the expression levels of the biomarkers (TCTP, EGFR, AKT, MCL1, and/or CXCL10).

In the present disclosure, it is found that biomarkers (TCTP, EGFR, AKT, MCL1, and/or CXCL10) serve as factors causing resistance to cancer immunotherapeutic agents and the resistance can be controlled by inhibiting or promoting the activity of the biomarkers. The use of the biomarkers (TCTP, EGFR, AKT, MCL1, and/or CXCL10) according to the present disclosure allows the prediction of resistance to or prognosis of a cancer immunotherapeutic agent and the selection of a therapy guaranteeing therapeutic benefit, thereby finding advantageous applications in treating cancers or tumors resistant to cancer immunotherapeutic agents.

BRIEF DESCRIPTION OF THE DRAWINGS

The above and other aspects, features and advantages of the present disclosure will be more apparent from the following detailed description taken in conjunction with the accompanying drawings, in which:

FIG. 1A is a view showing comparison of TPT1 expression between responders (R, n=68) and non-responders (NR, n=230). FIG. 1B is a view showing Kaplan-Meier analysis of overall survival and median expression cutoff values for the expression level of TPT1 (TPT1$^{high}$>median; TPT1$^{low}$<median, p=0.00822). FIG. 1C is a view showing CD8$^+$ T cell signature scores in TPT1$^{low}$ and TPT1$^{high}$ patients. FIG. 1D is a view showing anti-apoptosis signature scores in TPT1$^{low}$ and TPT1$^{high}$ patients.

FIG. 2B shows a schematic of the therapy regimen in BALB/c mice implanted with CT26 P0 or CT26 P3 cells (upper panel). FIGS. 2B, 2C, 2D and 2E show CT26 P3 cells transfected with the indicated siRNAs. FIG. 2C shows TCTP protein levels determined by Western blot analysis. FIG. 2D is a view showing transwell-based T cell chemotaxis assay. SiGFP- or siTPT1 #1, 2, 3-treated CT26 P3 cell-derived conditioned media (CM) was added to the lower chamber, and T cells were plated in the upper chamber. The T cells that migrated into the lower chamber were counted after 6 hours. FIG. 2E is a view illustrating that carboxyfluorescein succinimidyl ester (CFSE)-labeled tumor cells were exposed to tumor-specific CTLs and the frequency of CFSE+ apoptotic tumor cells was determined by flow cytometric analysis of active-caspase-3.

FIG. 2F is a schematic of the therapy regimen in BALB/c mice implanted with CT26 P3 cells. FIGS. 2G, 2H, 2I, 2J, 2K and 2L shows results of experiments in which CT26 P3 tumor-bearing mice were administered siGFP- or siTPT1- loaded chitosan nanoparticles (CNPs) with PD-L1 antibody. FIG. 2G shows tumor growth and FIG. 2H survival of mice inoculated with CT26 P3 cells treated with the reagents. FIG. 2I shows flow cytometry profiles of tumor-infiltrating CD8+ T cells. FIG. 2J shows tumor-infiltrating CD8+ T cell to CD4+, Foxp3+ Treg cell ratios. FIG. 2K shows the percentage of granzyme B+ cells in CD8+ T cells. FIG. 2L shows the frequency of apoptotic cells in the tumors. For the in vivo experiments, 10 mice from each group were used.

FIG. 3A shows levels of TCTP, CXCL10, and MCL-1 proteins as analyzed by Western blots. FIG. 3B shows data of T cell chemotaxis assays performed using CT26 No or CT26 TCTP cell-derived CM in the lower chamber and plating CD8+ T cells in the upper chamber. The T cells migrated into the lower chamber media were counted. FIG. 3C shows counts of the migrated T cells after incubation with empty vector- or CXCL10-transfected CT26 TCTP cell-derived CM.

FIGS. 3D and 3E show frequencies of CFSE+ apoptotic tumor cells as measured by flow cytometric analysis of active-caspase-3 after CFSE-labeled tumor cells were incubated with tumor-specific CTLs.

FIG. 3F is a schematic of the therapy regimen in BALB/c mice implanted with CT26 No or CT26 TCTP cells. FIGS. 3G, 3H, 3I, 3J, 3K and 3L show tumor-bearing mice treated or not treated with the PD-L1 antibody. FIG. 3G shows tumor growth of mice inoculated with CT26 No or TCTP cells treated with or without PD-L1 antibody and FIG. 3H shows survival of the mice. FIG. 3I shows flow cytometry profiles of tumor-infiltrating CD8+ T cells. FIG. 3J shows tumor-infiltrating CD8+ T cell to CD4+, Foxp3+ Treg cells ratios. FIG. 3K shows the percentage of granzyme B+ to tumor-infiltrating CD8+ T cells. FIG. 3L shows the frequency of apoptotic cells in the tumors treated with the indicated reagents. For the in vivo experiments, 10 mice from each group were used. The p-values by one-way ANOVA (3B)-(3D) and (3I)-(3L), two-way ANOVA (3G), and the log-rank (Mantel-Cox) test (3H) are indicated. The data represent the mean±SD.

FIG. 4B is a schematic of the therapy regimen in NOD/SCID mice implanted with A375 P0 or A375 P3 cells (upper panel) and shows TPT1 mRNA and TCTP protein levels in A375 cells at various stages of immune resistance as determined by qRT-PCR and Western blot analysis (lower panel). FIG. 4C shows the quantification of the frequency of TCTP+ tumor cells as analyzed by flow cytometry. FIG. 4D shows the protein levels of CXCL10 and MCL-1 as analyzed by Western blots. FIGS. 4E and 4G show data of experiments using A375 P3 cells transfected with the indicated siRNAs. In detail, FIG. 4E shows the protein levels of TCTP, CXCL10, and MCL-1 as determined by Western blot analysis. FIG. 4F shows data of transwell-based T cell chemotaxis assays performed by using SiGFP- or siTPT1-treated A375 P3 cell-derived conditioned media. FIG. 4G shows CFSE-labeled tumor cells exposed to tumor-specific CTLs and the frequency of CFSE+ apoptotic tumor cells (active-caspase-3) as determined by flow cytometry.

FIG. 4H is a schematic of the therapy regimen in NOD/SCID mice implanted with A375 P3 cells. FIGS. 4I, 4J, 4K, 4L and 4M show A375 P3 tumor-bearing mice administered siGFP- or siTPT1-loaded chitosan nanoparticles (CNPs) with or without NY-ESO1-specific T cell adoptive transfer treatment. FIG. 4I shows flow cytometry profiles of CFSE+ adoptively transferred NY-ESO1-specific T cells. FIG. 4J show the percentage of active-caspase-3+ apoptotic cells in the tumors treated with the indicated reagents. FIG. 4K show the frequency of apoptotic cells in the tumor relative to the NY-ESO1-specific T cells migrated to the tumor. FIG. 4L shows tumor growth of mice inoculated with A375 P3 cells treated with the indicated reagents and FIG. 4M shows survival of the mice. For the in vivo experiments, 10 mice from each group were used. The p-values by one-way ANOVA (FIGS. 4B, 4C, 4F, 4G, and 4I-4K), two-way ANOVA (FIG. 4L), and the log-rank (Mantel-Cox) test (FIG. 4M) are indicated. The data represent the mean±SD.

FIG. 5A shows the protein levels of EGFR, pEGFR, pAKT, AKT, MCL-1, and CXCL10 as measured by Western blot analysis. FIG. 5B shows the protein levels of pEGFR, EGFR, pAKT, AKT, MCL-1, and CXCL10 in SiGFP- or siEGFR-treated A375 TCTP cells as analyzed by Western blots. FIG. 5C shows data of experiments in which SiGFP- or siEGFR-treated A375 TCTP cell CM was added to the lower chamber, and CD8+ T cells were plated in the upper chamber. The T cells migrated into the lower chamber media were collected after 6 hours and counted. FIG. 5D shows the frequency of CFSE+ apoptotic tumor cells as determined by flow cytometric analysis of active-caspase-3 after CFSE-labeled tumor cells were exposed to NY-ESO1-specific CTLs.

FIGS. 5E, 5F, 5G and 5H illustrate A375 cells transfected with FLAG-TCTP wild type (TCTP), FLAG-TCTP S46A mutant, or FLAG-TCTP S46D mutant. FIG. 5E shows activation of EGFR, AKT signaling and expression of MCL-1 and CXCL10 as analyzed by Western blot assays. FIG. 5F shows data of T cell chemotaxis assays performed by using the indicated tumor cell-derived CM. FIG. 5G shows active caspase-3+ apoptotic tumor cells as analyzed by flow cytometry after incubation with CTLs. FIG. 5H shows cross-linked lysates immunoprecipitated with anti-Na, K ATPase antibody. The immunoprecipitated proteins were analyzed by Western blot assays. The numbers below the blot images indicate the expression as measured fold-change. The error bars represent mean±SD.

FIG. 6A shows data of the treatment of CT26 No and TCTP cells with the indicated concentrations of cisplatin, DHA, rapamycin, sertraline, and thioridazine for 24 hours, and IC$_{50}$ values. FIG. 6B shows results in term of the percentage of active-caspase3+ apoptotic tumor cells after CT26 TCTP cells were treated with the indicated agents, and incubated with tumor-specific CTLs at the indicated tumor:T cell ratio. FIG. 6C shows the combination score calculated based on changes in the percentage of apoptosis in drug-treated tumor cells with or without CTLs. Combination score=(% of active-caspase 3+ tumor cells by drug and CTLs)/(% of active-caspase 3+ tumor cells by drug).

Combination score=(% of active-caspase 3+tumor cells by drug and CTLs)/(% of active-caspase 3+tumor cells by drug).

Figure 6A:
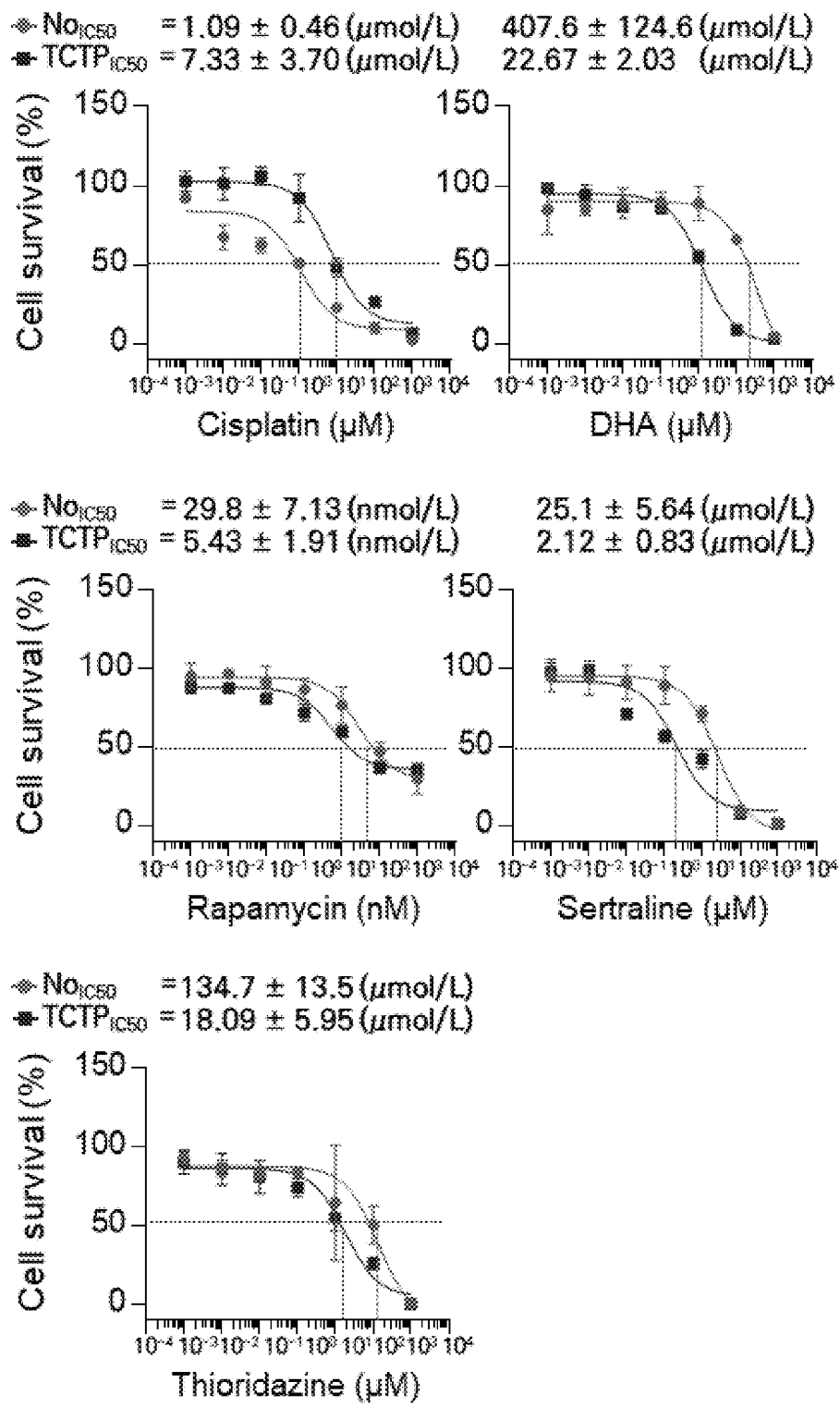
FIGS. 6A, 6B, 6C, 6D, 6E and 6F illustrate that inhibition of TCTP by DHA sensitizes TCTP$^{high}$ tumor cells to T cell-mediated killing and increases T cell migration.
Figure 6B:
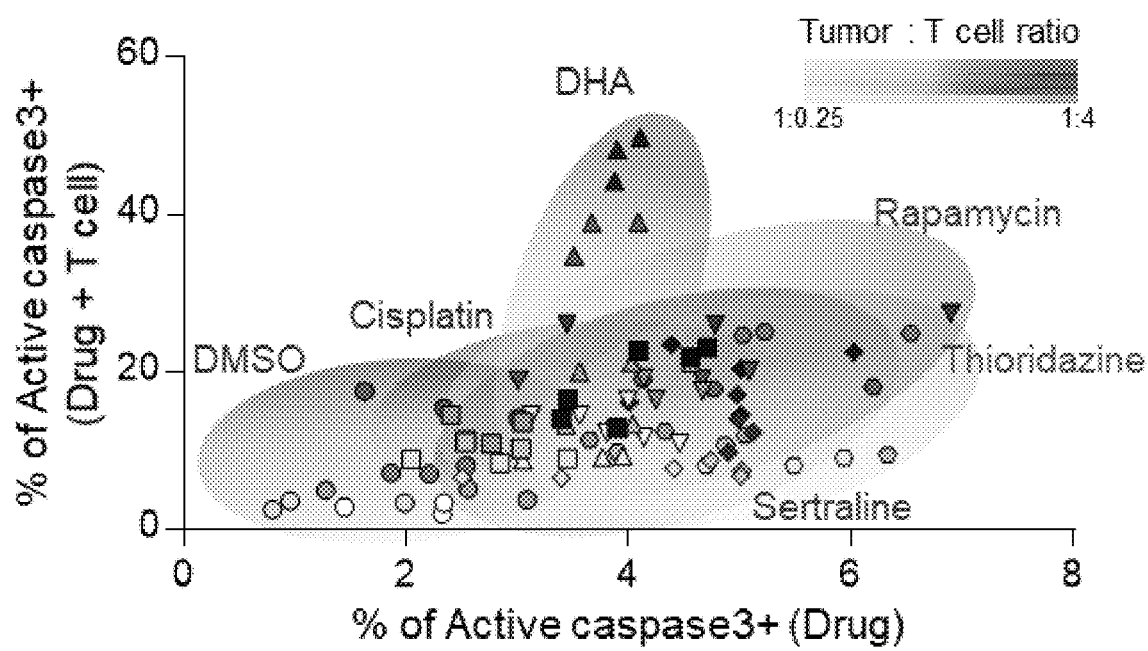
Figure 6C:
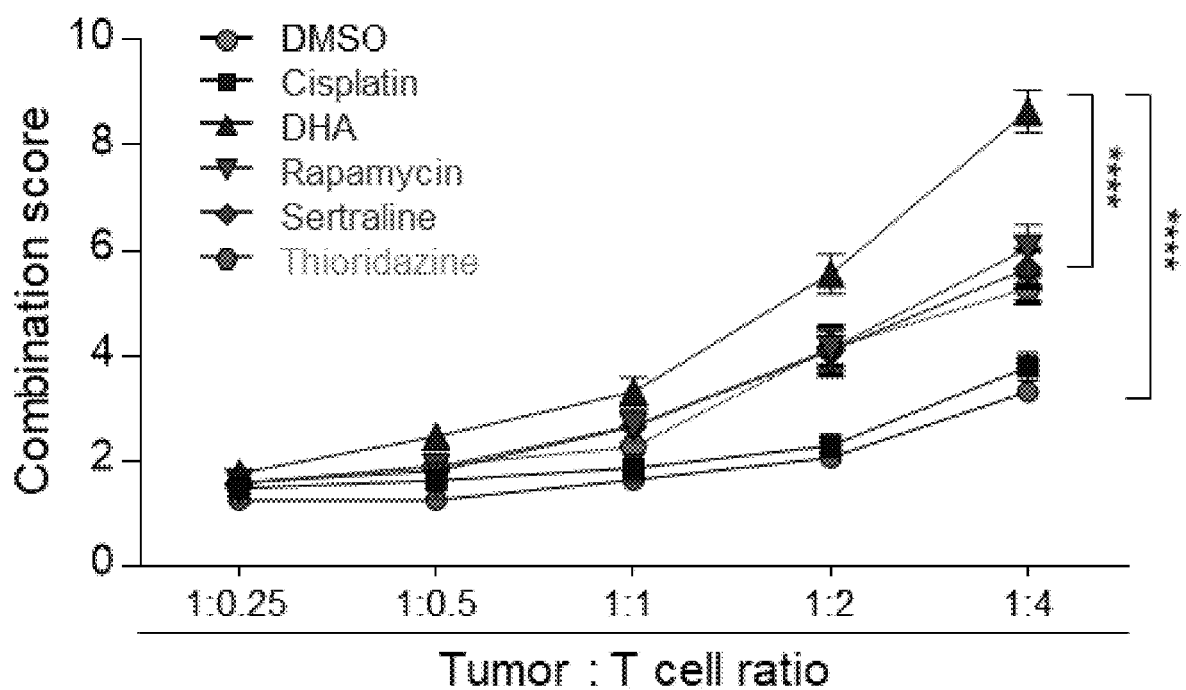
Figure 6D:
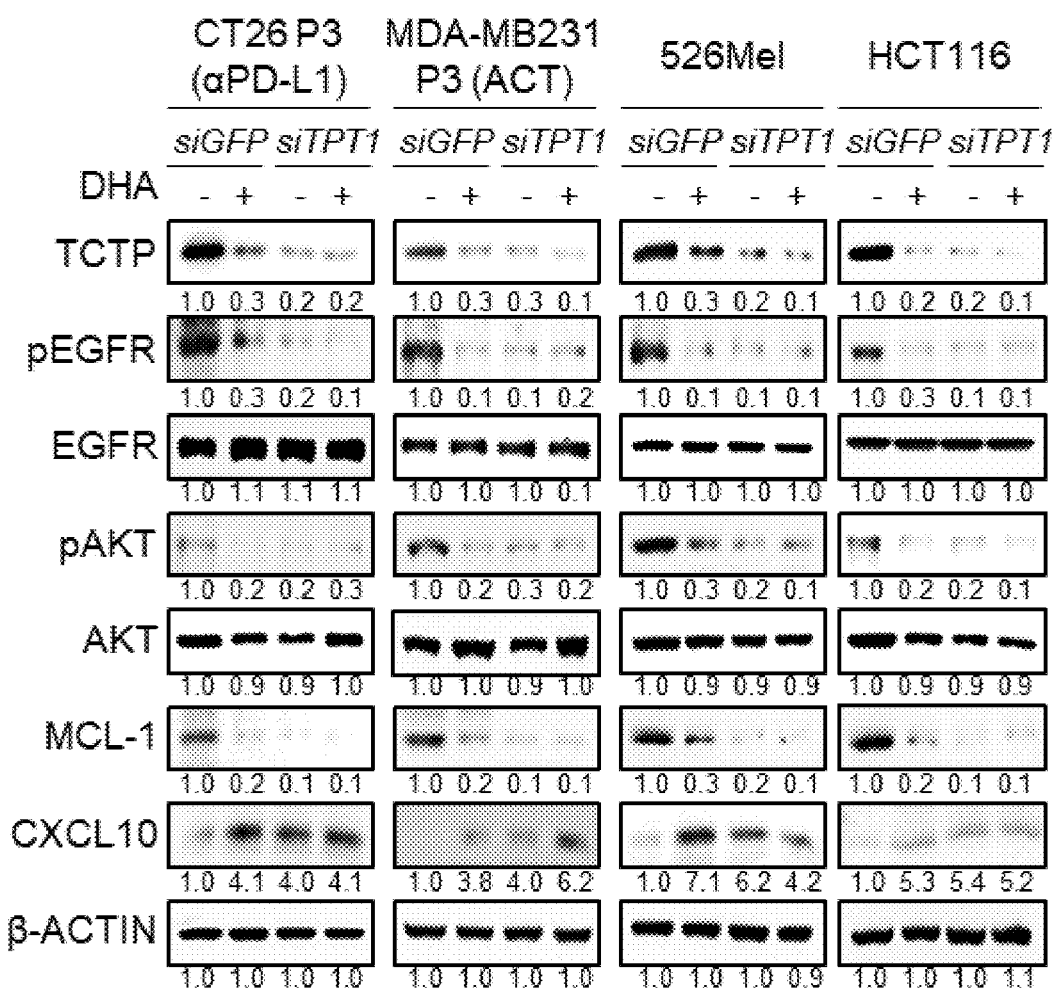
Figure 6E:
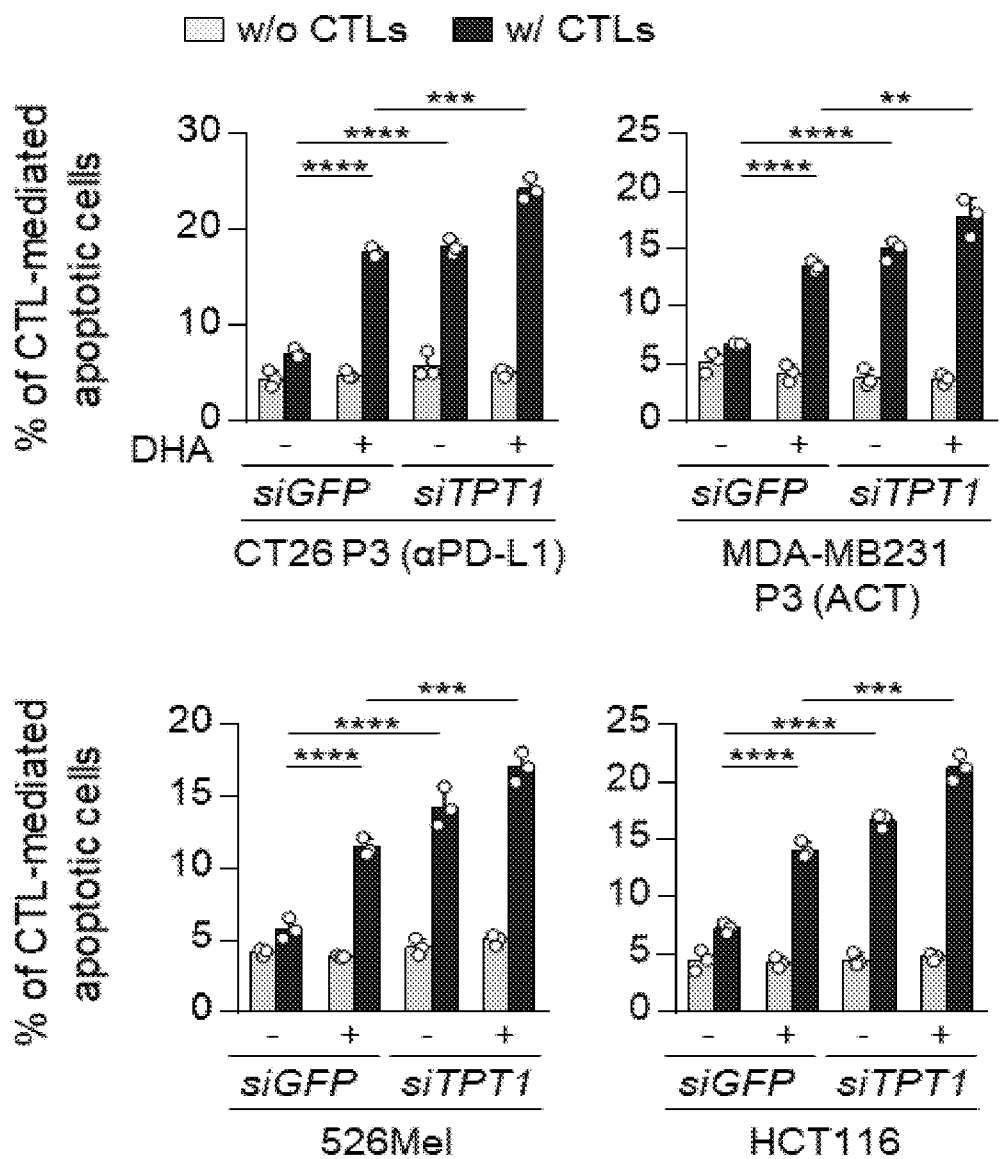
Figure 6F:
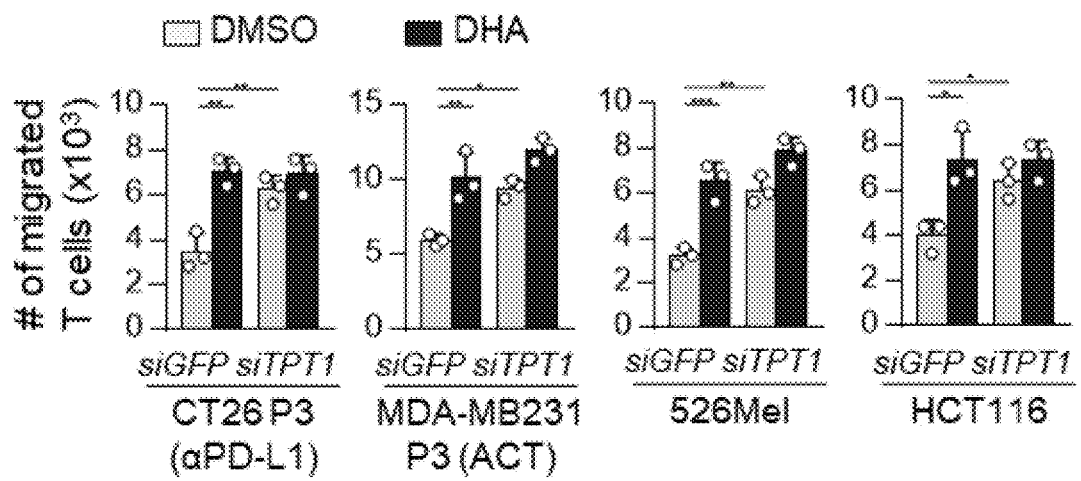

FIG. 6D shows results after SiGFP- or siTPT1-treated CT26 P3, MDA-MB231, 526Mel, and HCT116 cells were treated with PBS or DHA. The levels of TCTP, pEGFR, EGFR, pAKT, AKT, MCL-1, CXCL10, and β-ACTIN were analyzed by Western blots. FIG. 6E shows the percentage of CTL-mediated anti-apoptotic tumor cells as determined by flow cytometry. FIG. 6F shows data of T cell chemotaxis assays performed using PBS or DHA treated siGFP- or siTPT1-treated tumor cell CM. The numbers below the blot images indicate the expression as measured as fold change. The error bars represent mean±SD.

Figure 7A:
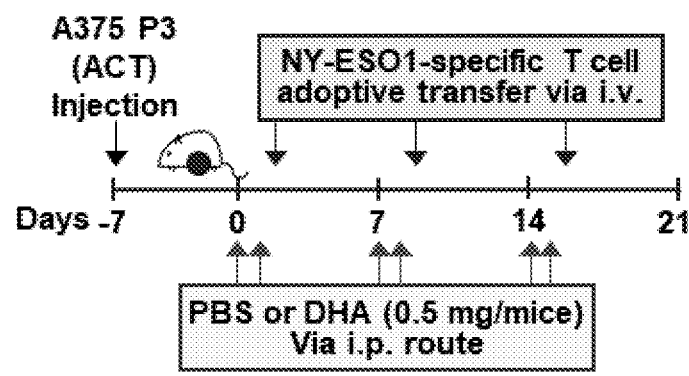
Figure 7B:
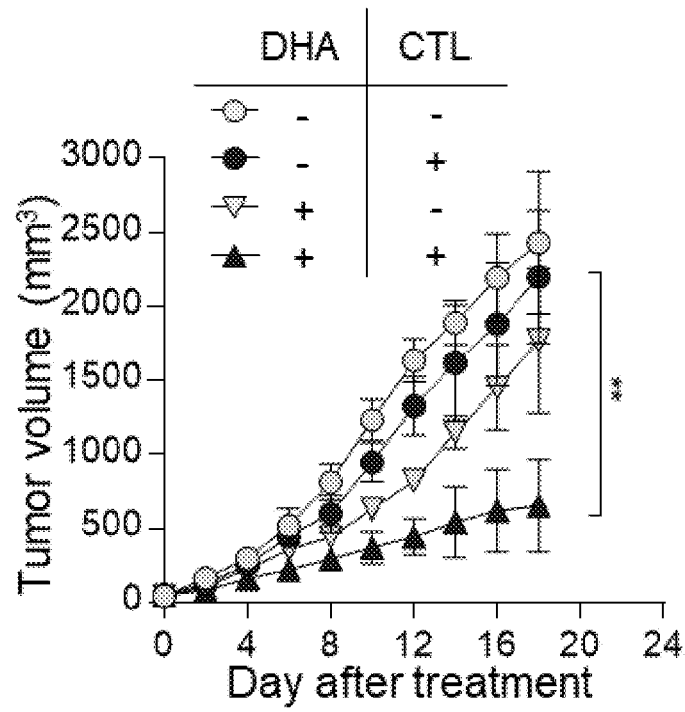
Figure 7C:
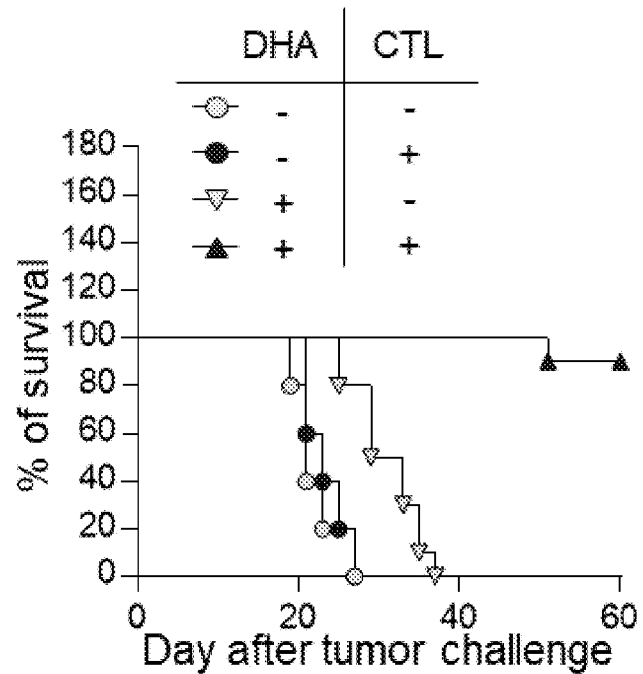
Figure 7D:
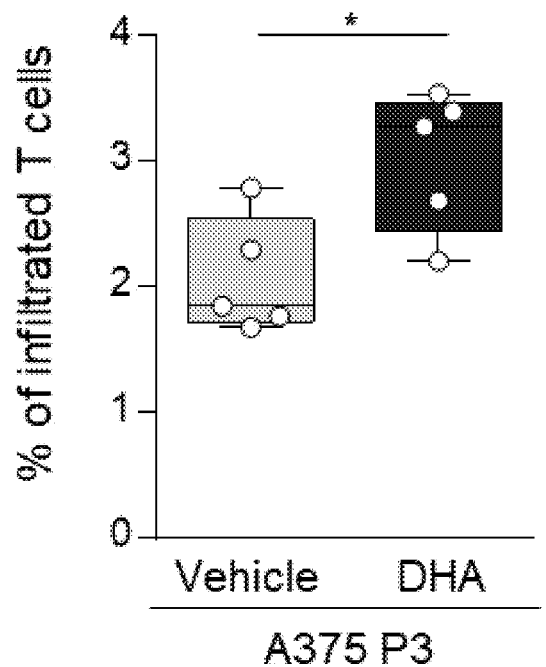
Figure 7E:
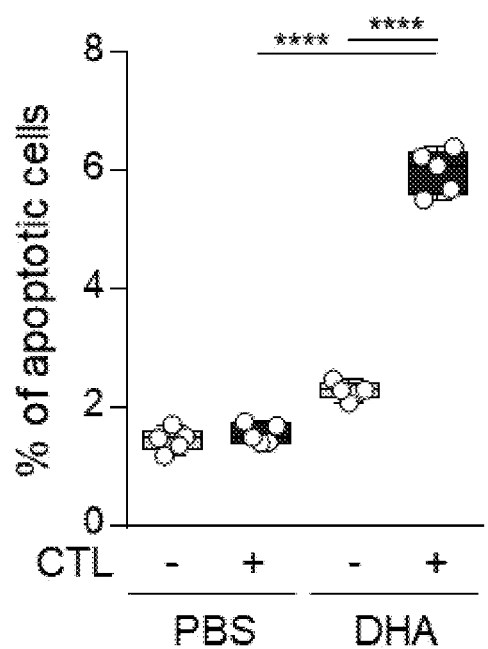
Figure 7F:
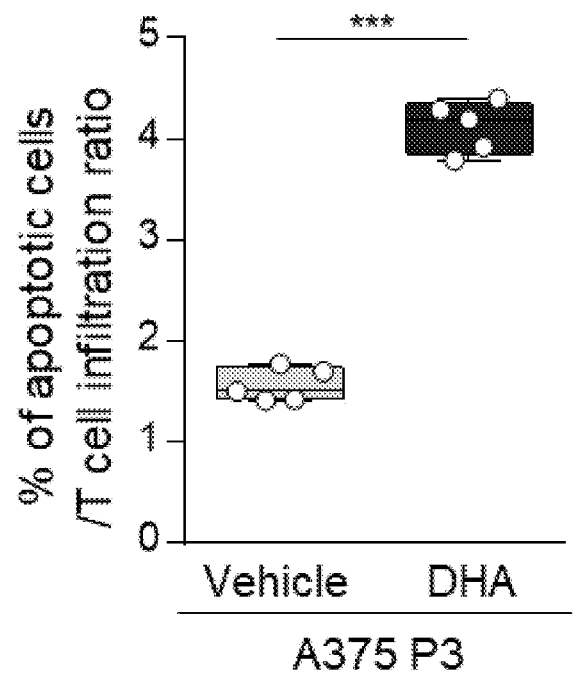

FIG. 7A. 7B and 7C show results indicating that therapeutic efficacy was increased when TCTP targeting by treatment of CT26 P3 with DHA in vivo was used in combination with PD-L1 antibody therapy. FIGS. 7D, 7E and 7F show results indicating that TCTP targeting increased counts of T cells in tumors and the apoptosis of cancer cells.

Figure 7G:
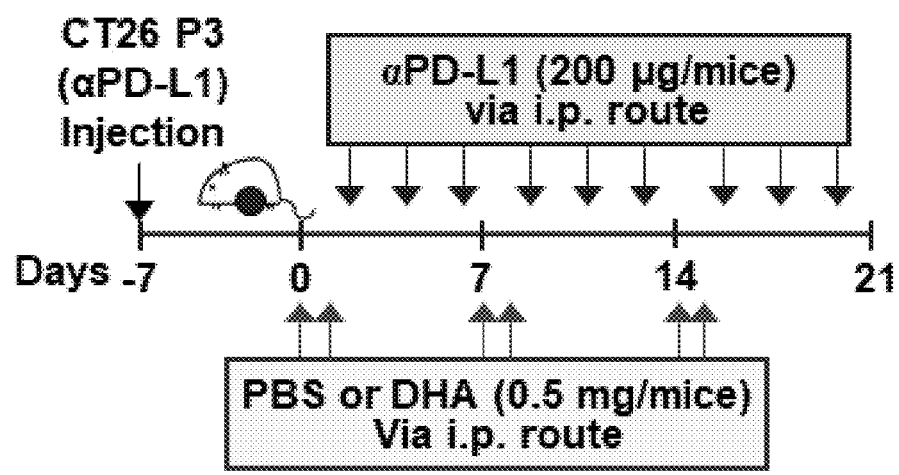
Figure 7H:
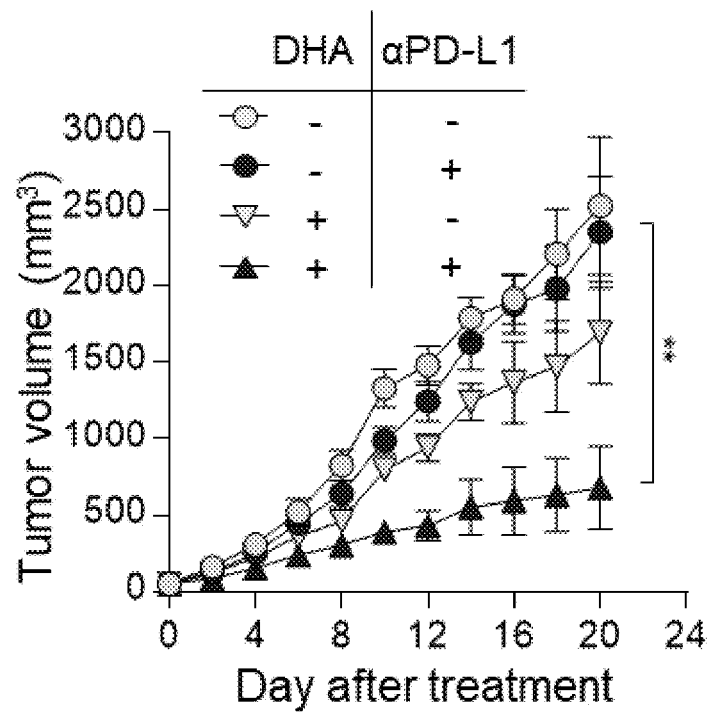
Figure 7I:
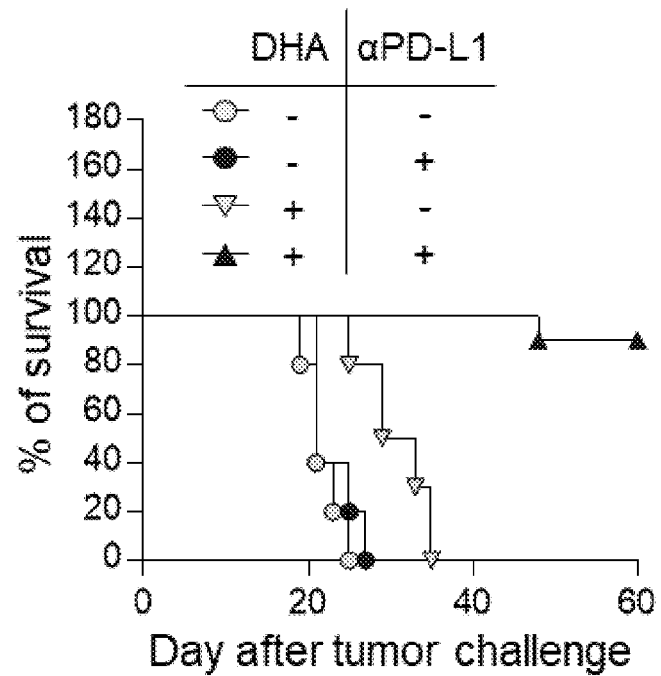
Figure 7J:
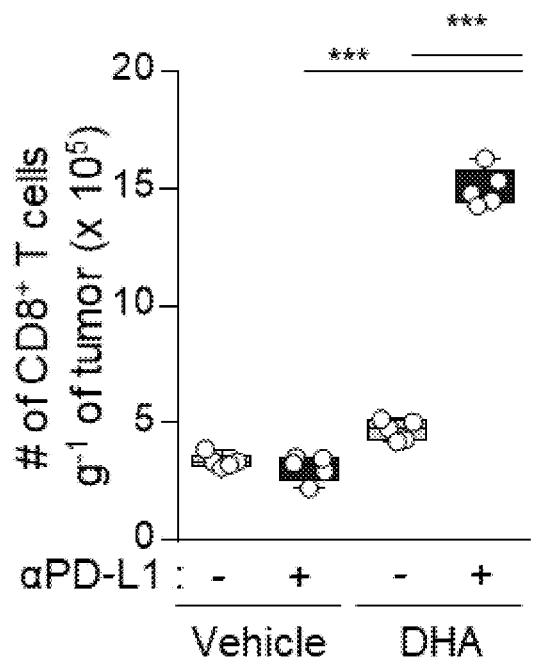
Figure 7K:
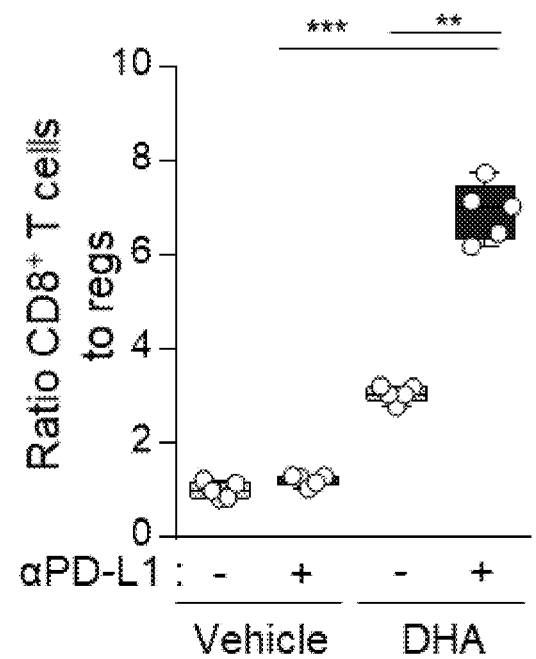
Figure 7L:
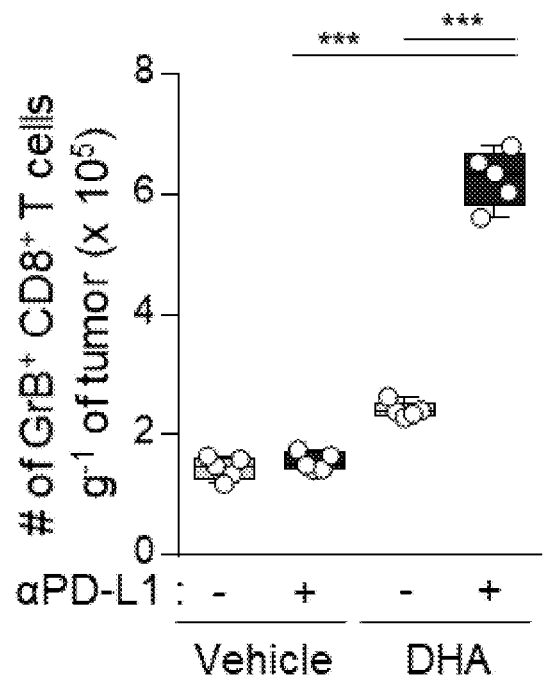
Figure 7M:
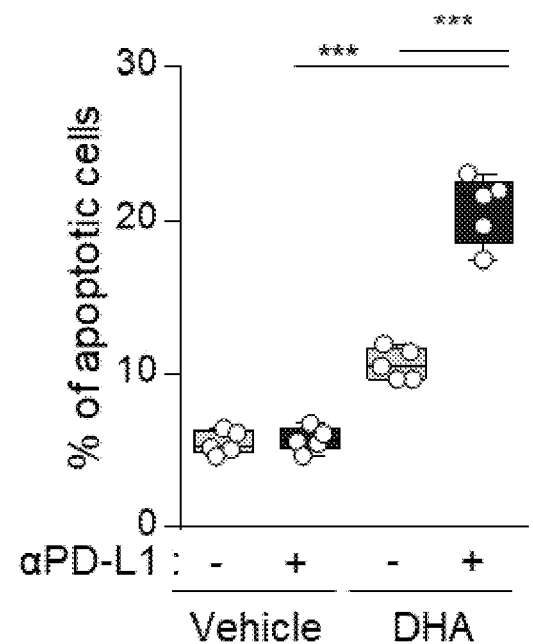

FIGS. 7G, 7H and 7I show results indicating that therapeutic efficacy was increased when TCTP targeting by treatment of CT26 P3 with DHA in vivo was used in combination with PD-L1 antibody therapy. FIGS. 7J, 7K, 7L and 7M show results indicating that TCTP targeting increased counts of T cells in tumors and the apoptosis of cancer cells.

Figure 8A:
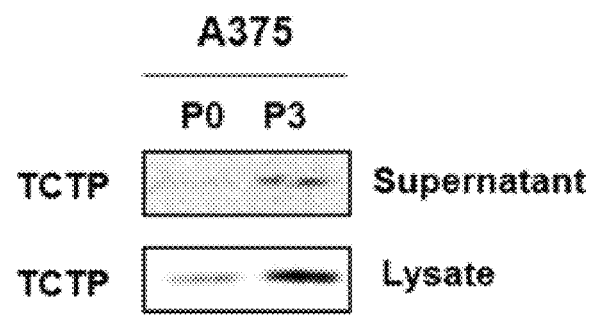
Figure 8B:
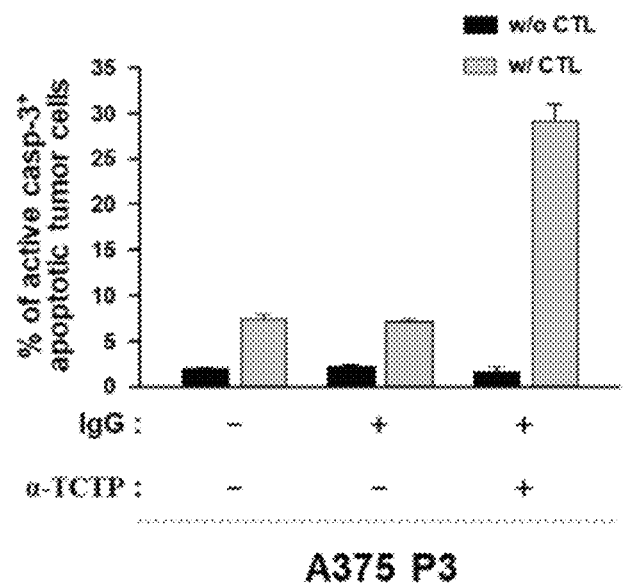
Figure 8C:
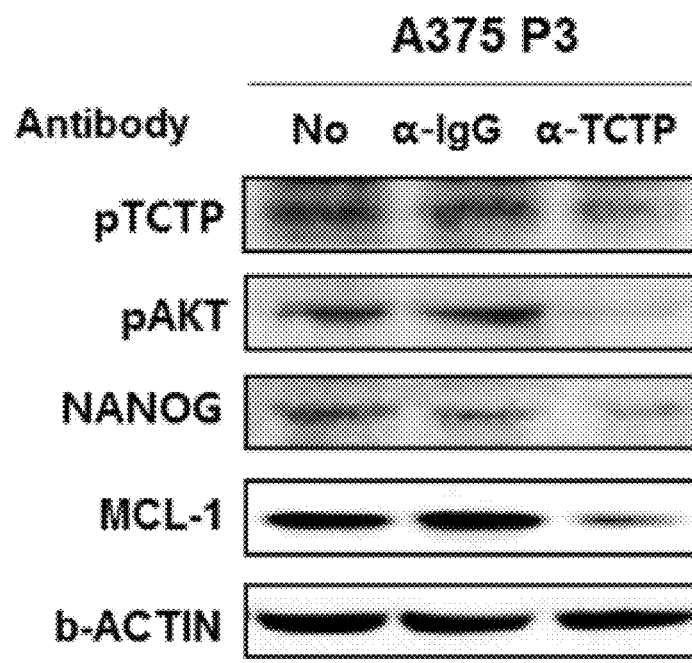

FIGS. 8A, 8B and 8C show results indicating that extracellular secretion of TCTP also increases in ACT-refractory A375 P3 and when a TCTP neutralizing antibody was used to target TCTP, phenotypes to anticancer immune resistance was decreased and the previously reported immune resistance and the expression of the cross resistance (cisplatin resistance) and multiple malignance (cancer metastasis and cancer stemness) regulator NANOG as well as the AKT signaling pathway were reduced. The data imply that the TCTP secreted outside tumor cells play a crucial role in the therapeutic resistance and multiple malignancy phenotypes of resistant cancer and the neutralization through an neutralizing antibody could reverse the phenotypes of resistant cancer.

Figure 9:
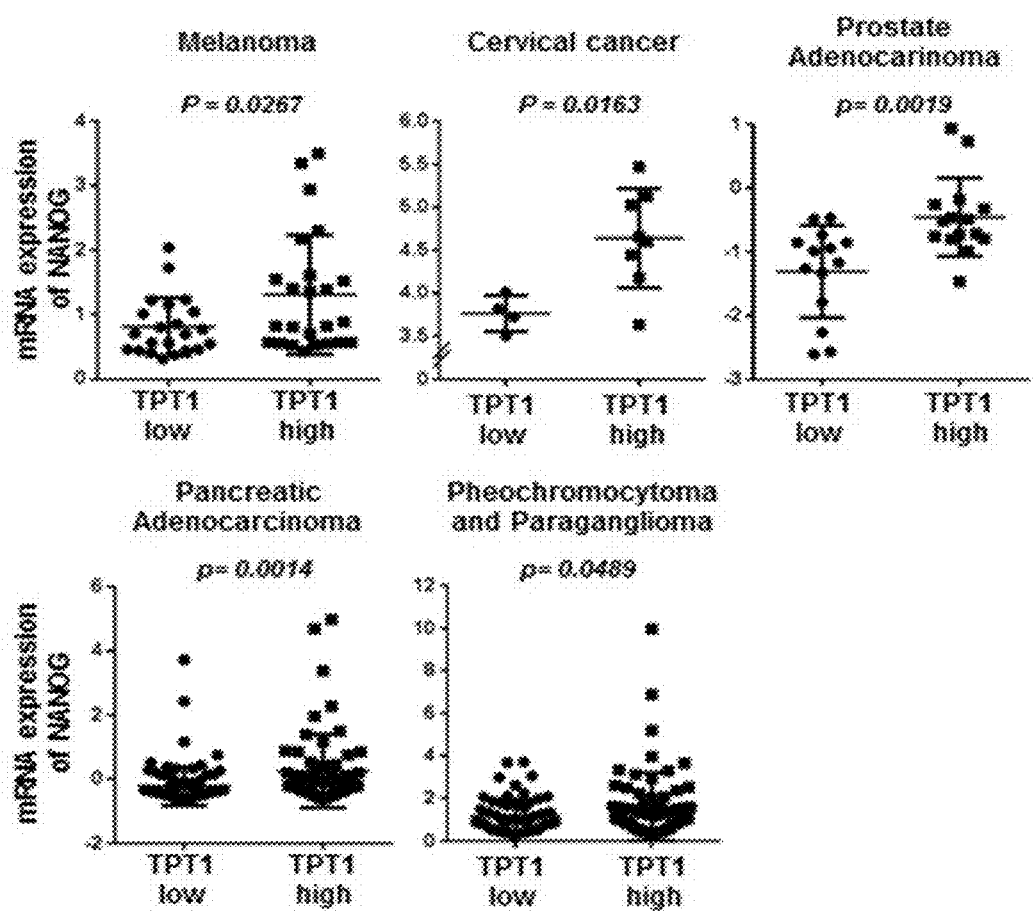

FIG. 9 shows results indicating that in samples of patients with various carcinomas, there is a significant correlation between immune resistance and the expression of NANOG, a factor regulating cross resistance (cisplatin resistance) and multiple malignancy (cancer metastasis and cancer stemness).

Figure 10:
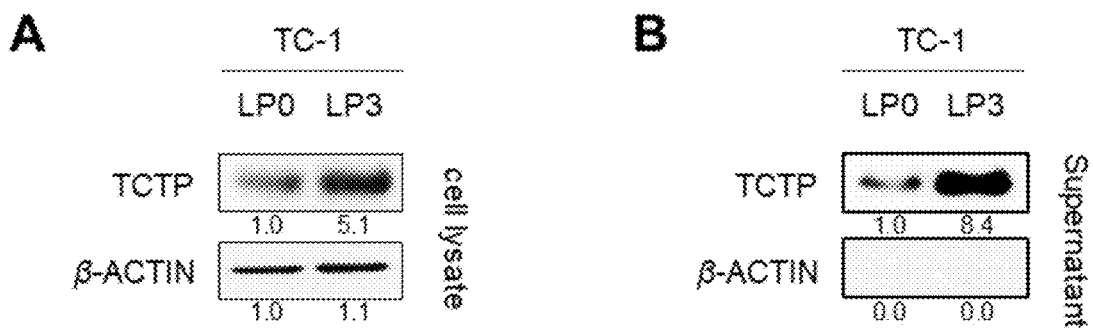

FIG. 10 shows results indicating that in the TC-1 LP3 constructed as an immune checkpoint antibody therapy-refractory orthostatic lung cancer model, intracellular and extracellular TCTP secretion remarkably increases.

Figure 11A:
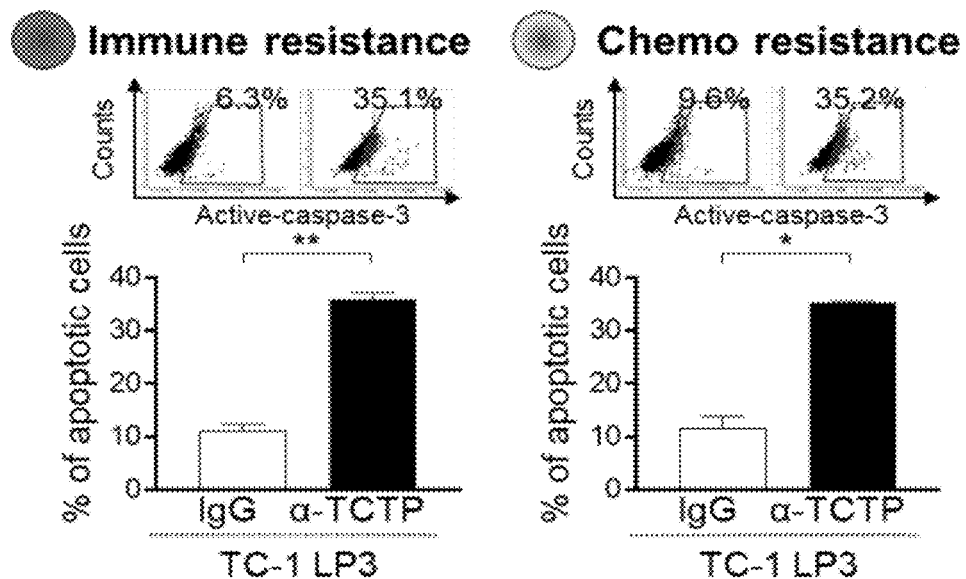
Figure 11B:
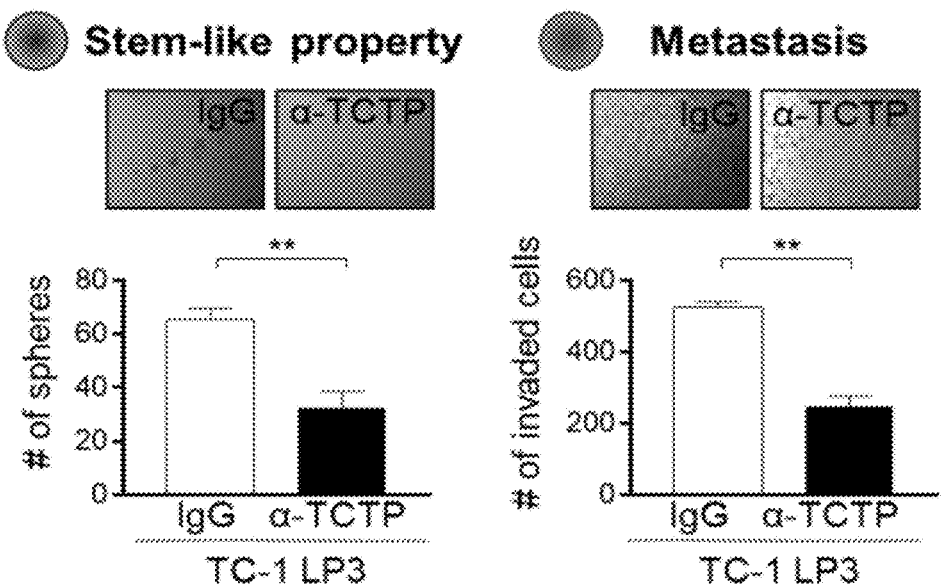

FIGS. 11A and 11B show results indicating that when TCTP was neutralized through an anti-TCTP neutralizing antibody, the previously reported immune resistance and cross resistance (cisplatin resistance) was decreased and multiple malignancy (cancer metastasis and cancer stemness) was also reduced.

DETAILED DESCRIPTION

A better understanding of the present disclosure may be obtained via the following examples which are set forth to illustrate, but are not to be construed as limiting the present disclosure.

EXAMPLES

Unless stated otherwise, "%", used to indicate concentrations of particular substances, stands for (wt./wt.) % for solid/solid, (wt./vol.) % for solid/liquid, and (vol./vol.) % for liquid/liquid throughout the specification.

Experimental Methods

Mice and Cell Lines

Female BALB/c and NOD/SCID mice at 6 to 8 weeks of age were purchased from Central Lab. Animal, Inc. (Seoul, Korea). All mice were handled and maintained under the protocol approved by the Korea University Institutional Animal Care and Use Committee (KUIACUC-2014-175). All animal procedures were performed in accordance with the recommendations for the proper use and care of laboratory animals.

A375, CaSki, 526Mel, MDA-MB-231, and HCT116 cells were obtained commercially from the American Type Culture Collection (ATCC, Manassas, VA, USA). All cell lines were purchased between 2010 and 2014 and tested for mycoplasma using a Mycoplasma Detection Kit (Thermo Fisher Scientific, San Jose, CA, USA). The identities of the cell lines were confirmed by short tandem repeat (STR) profiling by IDEXX Laboratories, Inc., and used within 6 months for testing.

To generate the A375/TCTP cells, pMSCV-TCTP plasmids were first transfected along with viral packaging plasmid (VSVG and Gag-pol) into HEK293FT cells. After three days, the viral supernatant was filtered through a 0.45 μm filter and introduced into A375 cells. Then, the infected cells were selected with 1 μg/ml puromycin. For the generation of the A375/P3 tumor line, $1 \times 10^6$ A375 cells were inoculated subcutaneously into NOD/SCID mice. After the initial tumor challenge, $2 \times 10^6$ NY-ESO1-specific CD8+ T cells and 3000 U of IL-2 (Novartis, Basel, Switzerland) were injected intravenously. After T cell adoptive transfer, the explanted tumor was expanded in vitro. This escape variant cell line was designated A375/P1 and injected into a new group of mice and selected by adoptive T cell transfer again. This treatment regimen was repeated for three rounds. All cells were grown at 37° C. in a 5% $CO_2$ humidified incubator chamber.

Chemical Reagents

The following chemical reagents were used in this study: BI2536 and cisplatin (Selleckchem, Houston, TX, USA). Dihydroartemisinin, sertraline hydrochloride, and rapamycin (Sigma-Aldrich, USA), and thioridazine (Tocris, UK).

DNA Constructs

DNA fragments of the TCTP gene were generated with a PCR-based strategy from genomic DNA extracted from A549 cells using primers (5'-GGATCCATGATTATC-TACCGGGAC-3' and 5'-CTCCAGTTAACATTTTTCCAT-TTCT-3') for the BamHI and XhoI sites. The BamHI and XhoI restriction fragments of the PCR product were subcloned into a pGEM-T vector (Promega, USA).

Site-Directed Mutagenesis

To generate mutations in the TCTP phosphorylation sites, the QuikChange Site-directed Mutagenesis Kit (Stratagene, San Diego, CA, USA) was used according to the manufacturer's instructions. In detail, the following primers were used (Table 1).

TABLE 1

| No. | Primer | Sequence (5' to 3') | SEQ ID NO: |
|---|---|---|---|
| 1 | TCTP S46D forward | GGTAACATTG ATGACGACCT CATTGGTGGA AATGCCTCCG C | 1 |

TABLE 1-continued

| No. | Primer | Sequence (5' to 3') | SEQ ID NO: |
|---|---|---|---|
| 2 | TCTP S46D reverse | GCGGAGGCAT TTCCACCAAT GqAGGTCGTC ATCAATGTTA CC | 2 |
| 3 | TCTP S46A forward | CGAGGGCGAA GGTACCGAAG CAACAGTAAT CACTGGTGTC G | 3 |
| 4 | TCTP S46A reverse | CGACACCAGT GATTACTGTT GCTTCGGTAC CTTCGCCCTC G | 4 |

The PCR thermal cycling conditions were 95° C. for 5 minutes; 18 cycles of 95° C. for 1 minute, and 64° C. for 1 minute, and 68° C. for 15 minutes. The PCR products were digested with Dpn I at 37° C. for 1 hour and transformed into XL10-Gold ultracompetent bacterial cells. Mutations were confirmed through DNA sequencing.

Real-Time Quantitative RT-PCR

Total RNA from the cells was purified using a RNeasy Micro kit (Qiagen, Valencia, CA, USA) and cDNA was synthesized by reverse transcriptase (RT) using an iScript cDNA synthesis kit (Bio-Rad, Hercules, CA, USA) according to the manufacturer's recommended protocol. Real-time PCR was performed using iQ SYBR Green Super mix (Bio-Rad) with the specific primers on a CFX96 real-time PCR detection system. All experiments were performed in triplicate and the quantification cycle (Cq) values were measured using Bio-Rad CFX 96 Manager 3.0 software.

Predesigned QPCR primers were purchased from Bioneer (South Korea).

TABLE 2

| No. | Primer | Sequence (5' to 3') | SEQ ID NO: |
|---|---|---|---|
| 1 | TPT1 forward | ATGACGAGCT GTTCTCCGAC | 5 |
| 2 | TPT1 reverse | AACACCGGTG ACTACTGTGC | 6 |

Relative quantifications of the mRNA levels were performed using the comparative Ct method with beta-actin as the reference gene. Fold-change was calculated relative to the expression level of mRNA in the control cells.

siRNAs Constructs

Synthetic small interfering RNAs siGFP, siTPT1, and siEGFR were purchased from Bioneer (South Korea), and had the following sequences.

TABLE 2

| No. | siRNA name | Sequence Sequence (5' to 3') | SEQ ID NO: |
|---|---|---|---|
| 1 | GFP sense | GCAUCAAGGUGAACUUCAA | 7 |
| 2 | GFP antisense | UUGAAGUUCACCUUGAUGC | 8 |
| 3 | mouse TPT1 #1 sense | GAAAUCACUCAAAGGCAAA | 9 |
| 4 | mouse TPT1 #1 antisense | UUUGCCUUUGAGUGAUUUC | 10 |
| 5 | mouse TPT1 #2 sense | CUGUUCUCCGACAUCUACA | 11 |
| 6 | mouse TPT1 #2 antisense | UGUAGAUGUCGGAGAACAG | 12 |
| 7 | mouse TPT1 #3 sense | AGCACAUCCUUGCUAAUUUTT | 13 |
| 8 | mouse TPT1 #3 antisense | AAAUUAGCAAGGAUGUGCUTA | 14 |
| 9 | human TPT1 sense | GCAUGGUUGCUCUAUUGGA | 15 |
| 10 | human TPT1 antisense | UCCAAUAGAGCAACCAUGC | 16 |
| 11 | human EGFR sense | AGGAAUUAAGAGAAGCAACAU | 17 |
| 12 | human EGFR reverse | AUGUUGCUUCUCUUAAUUCCU | 18 |
| 13 | mouse MCL-1 sense | GGGCAGGAUUGUGACUCUUAUUUCU | 19 |
| 14 | mouse MCL-1 antisense | AGAAAUAAGAGUCACAAUCCUGCCC | 20 | siRNA was delivered into 6-well plates at a dose of 200 pmol/well using Lipofectamine 2000 (Invitrogen, Carlsbad, CA, USA) in vitro. siRNA was delivered into mice after formulation with chitosan nanoparticles. Briefly, siRNA (1 µg/ul) and tripolyphosphate (0.25% w/v) were combined in RGD-chitosan solution, and the mixture was incubated at 4° C. for 40 minutes. siRNA-loaded nanoparticles were purified by centrifugation and injected into the tail veins of tumor-bearing mice.

Granzyme B Apoptosis Assays

Granzyme B (Enzo Life Sciences, NY, USA) was delivered into cells by the BioPORTER QuikEasy Protein Delivery Kit (Sigma-Aldrich, St. Louis, MO, USA). Tumor cells ($5 \times 10^4$) were plated in 12-well plates and cultured overnight at 37° C. The cells were washed and 200 ng of granzyme B with BioPORTER in Opti-MEM was added to each well. After incubation for 4 hours, the frequency of apoptotic cells was determined by staining with anti-active caspase-3 antibody and analyzed by flow cytometry.

In Vitro CTL Assays

The tumor cells were harvested by trypsinization and washed once with DMEN (Thermo Fisher, USA) containing 0.1% fetal bovine (FBS), resuspended, and labeled in 0.1% DMEN with 10 µM CFSE for 10 minutes in a 37° C. incubator with 5% $CO_2$. Then, the CFSE-labeled (MCF-7, HCT116, CaSki, MDA-MB-231) tumor cells were resuspended in 10 µM MART-1 peptide containing 1 ml of DMEM. In the case of A375 and 526Mel, the peptide-pulsing process was not needed. After peptide-pulsing for 1 hour, the cells were incubated for 4 hours with MART-1- or the NY-ESO1-specific CD8+ T cell lines at an E/T ratio of 1:1. The frequency of apoptotic cells was analyzed by staining with anti-active caspase-3 antibody and performing flow cytometry. All analysis was performed using a Becton Dickinson FACSverse (BD Bioscience, USA).

In Vitro Transwell-Based T Cell Chemotaxis Assays

T cells were applied at $1 \times 10^5$ cells/well to the upper wells of 3.0 µm 24-well cell culture inserts (Corning Lowell, MA, USA). The wells were filled with tumor cell-derived conditioned media (CM). After 4 hours of incubation at 37° C., the migrated T cells were collected from the bottom wells and counted by flow cytometry.

Cell Viability Assays

CT26 tumor cells were treated with indicated concentrations of cisplatin, dihydroartemisinin, rapamycin, sertraline, and thioridazine for 24 hours. Cell viability was measured by the trypan blue exclusion assay, and the concentrations causing a 50% decrease in cell viability ($IC_{50}$ values) were determined.

Gene Set Used for Signatures

Because KEGG pathways often include large numbers of genes with only loosely related functions, the present inventors constructed two core, refined gene sets. Specifically:
CD8+ T-effector signature genes
anti-apoptosis signature genes, the present inventors used the genes within the negative regulation of apoptotic processes.

Gene Set Used for Signatures

For gene expression analysis, the expression of each gene in a signature was first z-score-transformed. Then, a principal component analysis was performed for expression values of T cell signature genes (CD8A, CD8B, CXCL10, CXCL9, GZMA, GZMB, IFNG, PRF1, TBX21) and anti-apoptotic signature genes (IL1RAP, IRAK2, IRAK3, PPP3CA, PRKAR2B, CHP1, CHP2, TNFRSF10B, IKBKG, CFLAR, PIK3R1, FAS, XIAP, CYCS, BCL2), and PC1 (principal component 1) was extracted to serve as a gene signature score.

In Vivo Tumor Treatment Experiments

To characterize the in vivo resistance to anti-PD-L1 conferred by TCTP, BALB/C mice were inoculated subcutaneously with $1 \times 10^5$ CT26 tumor cells per mouse. Seven days following tumor challenge, siGFP- or siTPT1-loaded chitosan nanoparticles (5 µg/animal) was administered via intravenous injection for a day before anti-PD-L1 (BioXcell, NH, USA) (200 µg/m ice).

In addition, to characterize the in vivo resistance to CTL killing conferred by TCTP, NOD/SCID mice were inoculated subcutaneously with $1 \times 10^6$ A375 tumor cells per mouse. Seven days following tumor challenge, siGFP- or siTPT1-loaded chitosan nanoparticles (5 µg/animal) was administered via intravenous injection for a day before adoptive transfer with NY-ESO1-specific CTLs. This treatment protocol was repeated for 3 cycles. The mice were monitored for tumor burden and survival for 26 and 76 days after the challenges, respectively.

Statistics

All data shown are representative of at least three separate experiments. Comparisons between individual experimental data points were made using the 2-tailed Student's t test. All p-values of <0.05 were considered statistically significant.

Example 1: Correlation of TCTP with Poor Response to Anti-PD-L1 Therapy

Figure 1A:
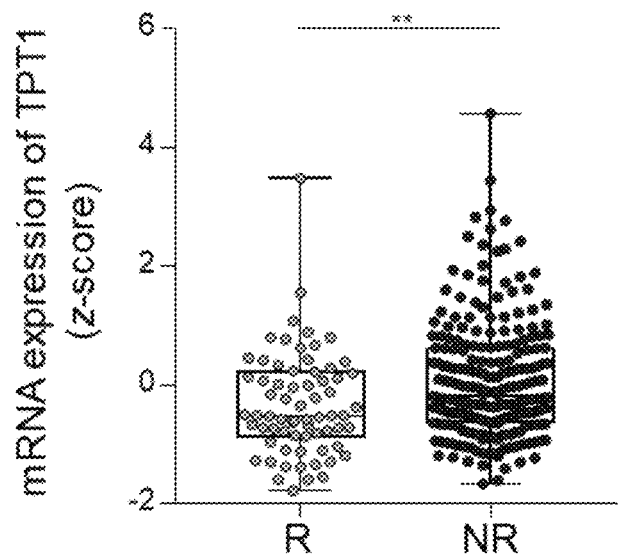
FIGS. 1A, 1B, 1C and 1D illustrate that increased expression of TPT1 is associated with a non-responder phenotype to anti-PD-L1 therapy.

To determine the clinical relevance of TCTP in response to outcomes of ICB (immune checkpoint blocker) therapy, the present inventors used the transcriptome data from metastatic urothelial cancer (mUC) patients classified as responders (R) or non-responders (NR) to anti-PD-L1 therapy. From the comparative transcriptome analysis of the differentially expressed genes (DEGs) in the two patient groups, it was found that the expression level of TPT1 (encoding TCTP) was significantly higher in the NR compared to the R (FIG. 1A).

Figure 1B:
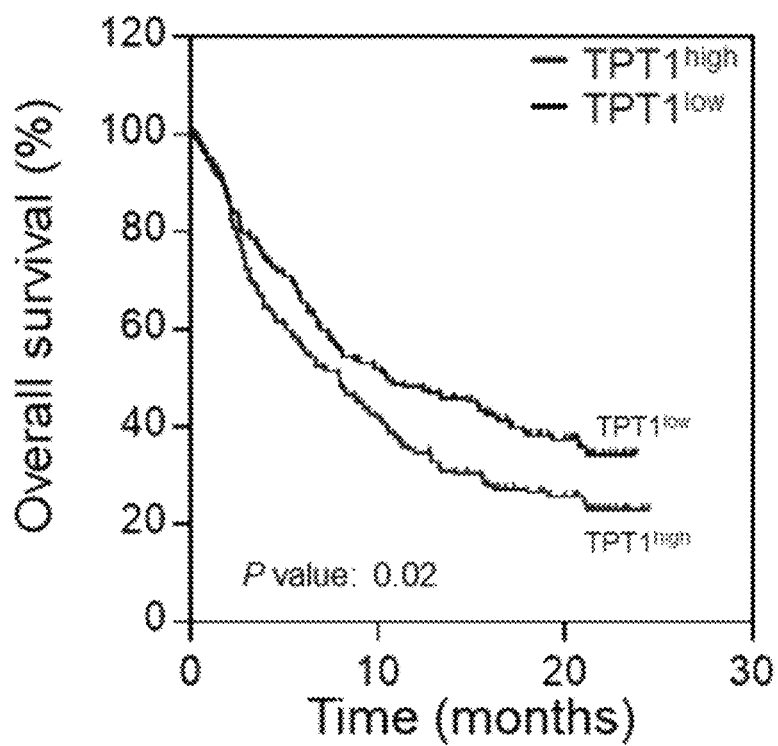

In addition, patients with high TPT1 expression in their tumors (TPT1$^{high}$) had poor prognosis compared to patients with low TPT1 expression (TPT1$^{low}$) ($p<0.02$) (FIG. 1B), indicating that the expression of TPT1 was associated with poor response to anti-PD-L1 therapy and survival outcomes of patients.

Figure 1C:
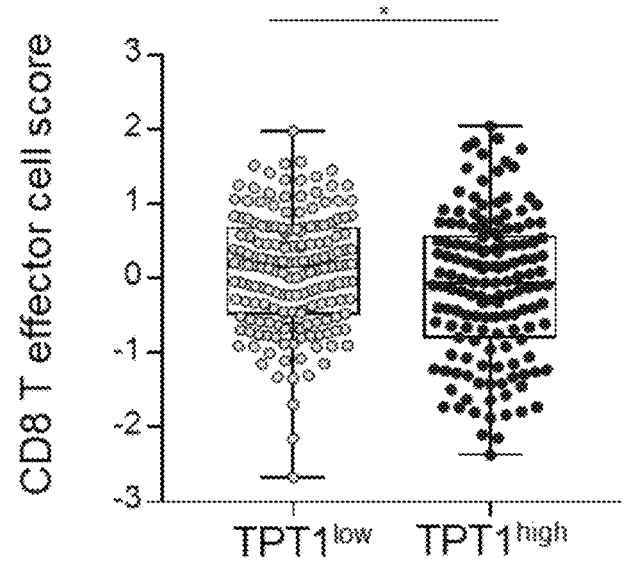

Then, the present inventors questioned whether TCTP is responsible for anti-PD-L1 therapy refractory properties. It has been reported that multi-gene signatures are associated with the clinical efficacy of ICB therapy. In this regard, the response outcomes to ICB therapy are predictable by evaluating the functionality of infiltrated CD8+ T cells that can be measured most robustly via the expression of CD8+ T cell signature genes. Interestingly, the present inventors found that TPT1 expression was inversely correlated with T cell infiltration in the patients (FIG. 1C).

That is, the higher the expression level of the TPT1 gene is, the lower are the survival rate of the patients and the index of T cell counts in tumor.

Figure 1D:
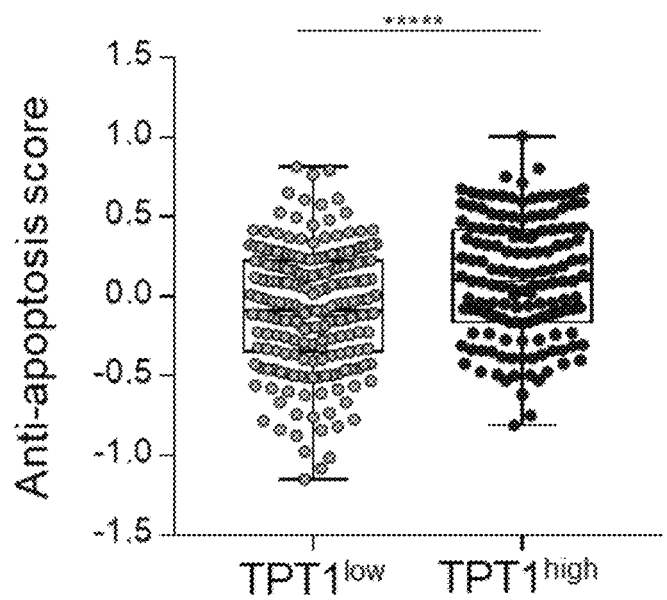

One of the major obstacles to successful cancer immunotherapy is the intrinsic resistance of tumor cells to CTL-mediated apoptosis. The intrinsic resistance of tumor cells to CTL-mediated apoptosis is characterized by the gene signature responsible for the anti-apoptosis pathway. Indeed, the anti-apoptosis signature was higher in NR compared to R to anti-PD-L1 therapy and positively correlated with TPT1 expression (FIG. 1D).

Taken together, these results strongly indicate that TPT1 mRNA expression is highly associated with immune-refractory phenotypes including non-T cell inflamed tumors and resistance to CTL-mediated killing. Therefore, TPT1 could be a biomarker in predicting the response to anti-PD-L1 therapy and clinical outcomes.

Example 2: Requirement of TCTP for Immune-Refractoriness to Anti-PD-L1 Therapy and Reversal of Immune-Refractoriness Through TCTP Gene Expression Suppression To explore the mechanisms responsible for the refractory phenotypes of tumors to ICB therapy, the present inventors newly developed an ICB-refractory CT26 P3 tumor model generated from an ICB-susceptible parental cell line, CT26 P0, through three rounds of in vivo selection by anti-PD-L1 therapy (FIG. 2A).

Figure 2A:
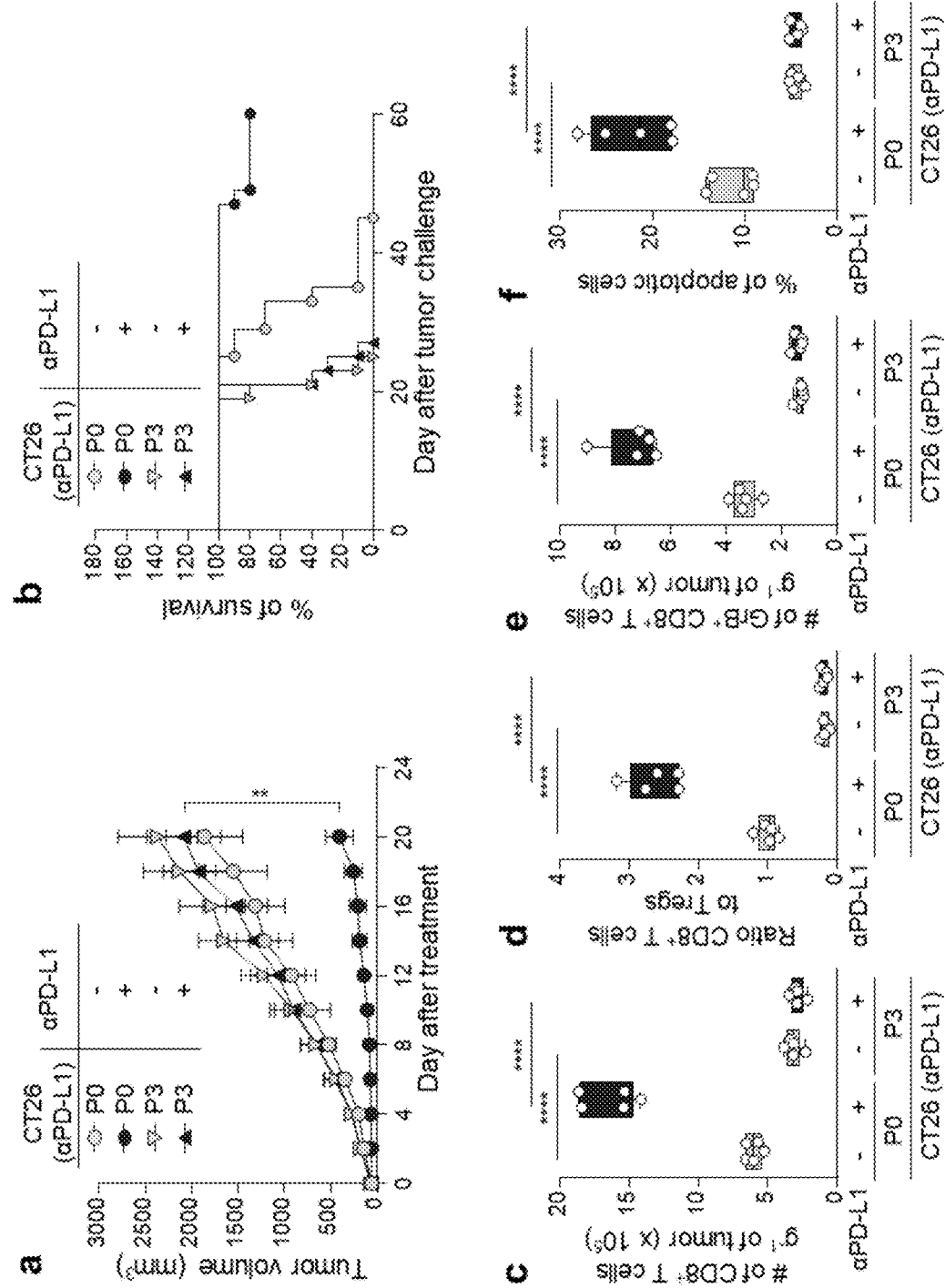
FIG. 2A shows results of the establishment of CT26 P3-implanted mouse model resistant to PD-L1 antibody therapy (A and B) and lower levels of CD8+ T cell counts in tumor (C-E) and apoptosis of cancer cells (F), compared to mother cell line CT26 P0 in the cancer resistant model.

While anti-PD-L1 antibody treatment successfully retarded tumor growth and prolonged mouse survival in CT26 P0 tumor-bearing mice, there was no remarkable therapeutic effects in CT26 P3 tumor-bearing mice (FIGS. 2A A-B). As evidenced by decreased levels of overall CD8+ T cells, the ratio of CD8+ T cells to T regs and tumor-reactive CD8+ T cells making granzyme B P3 tumors exhibited non-T cell inflamed immune phenotypes, relative to CT26 P0 tumors, (FIG. 2A C-F).

Notably, anti-PD-L1 therapy significantly induced T cell-inflamed immune phenotypes and apoptotic cell death in the CT26 P0 tumors. However, refractoriness appeared in CT26 P3 tumors, and these refractory phenotypes of CT26 P3 tumors were not reversed by PD-L1 blockade (anti-PD-L1).

Thus, these data indicate that the refractory properties to anti-PD-L1 therapy shown in patients were conserved in our ICB-refractory tumor model constructed by the present inventors.

Figure 2B:
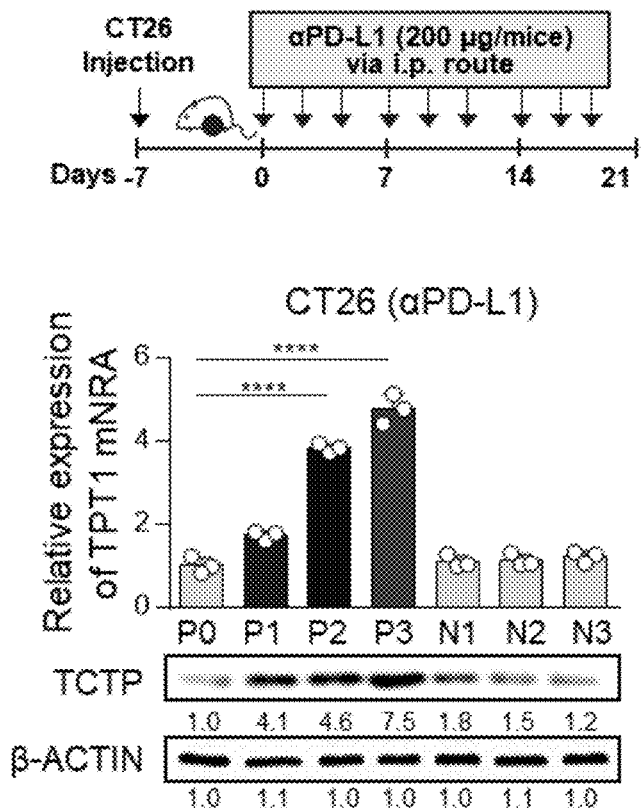
FIGS. 2B, 2C, 2D, 2E, 2F, 2G, 2H, 2I, 2J, 2K and 2L are views illustrating that silencing TCTP reverses tumor intrinsic resistance to CTL-mediated cell killing and the non-T cell inflamed tumor microenvironment of immune-refractory cancer.

To characterize the role of TCTP in ICB-refractory properties, the present inventors constructed a CT26 P3 tumor model by performing three rounds of in vivo selection through anti-PD-L1 therapy and measured the levels of TCTP mRNA and protein in different rounds of selection by anti-PD-L1 therapy (P0 to P3) or IgG treatment (N1 to N3), and found a stepwise increase in the levels of TCTP from P0 to P3 (FIG. 2B).

On the basis of the fact that tumor cells could regulate T cell trafficking, the present inventors performed an in vitro Transwell-based chemotaxis assay and found that CT26 P3 cells had a much lower capacity to recruit the T cells compared to CT26 P0 cells. Furthermore, the present inventors tested T cell chemotaxis by using conditioned media (CM) derived from CT26 P0 or P3 cells and observed that CT26 P3-derived CM markedly reduced T cell chemotaxis compared to CM from P0 cells (FIG. 2D). These results suggest that ICB-refractory CT26 P3 cells could inhibit T cell infiltration by decreasing the production of soluble factors responsible for T cell chemotaxis.

Figure 2C:
Figure 2D:
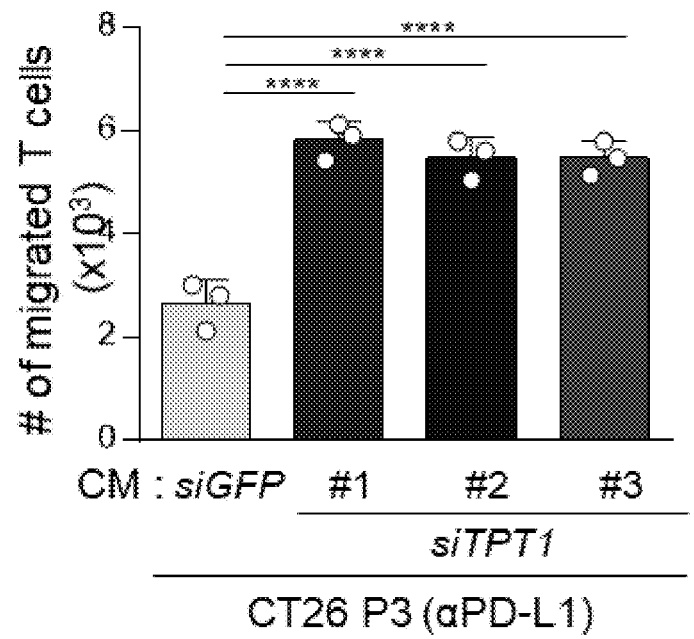

In order to confirm the direct association of TCTP gene with ICB-refractory phenotypes of CT26 P3 tumor cells, siRNA (siTPT1 #1, #2, #3) was used to silence TPT1 in CT26 P3 cells (FIG. 2C).

Notably, T cell migration was increased when incubated with CM derived from siTPT1-transfected CT26 P3 cells, compared to siGFP-transfected CT26 P3 cells (FIG. 2D).

Figure 2E:
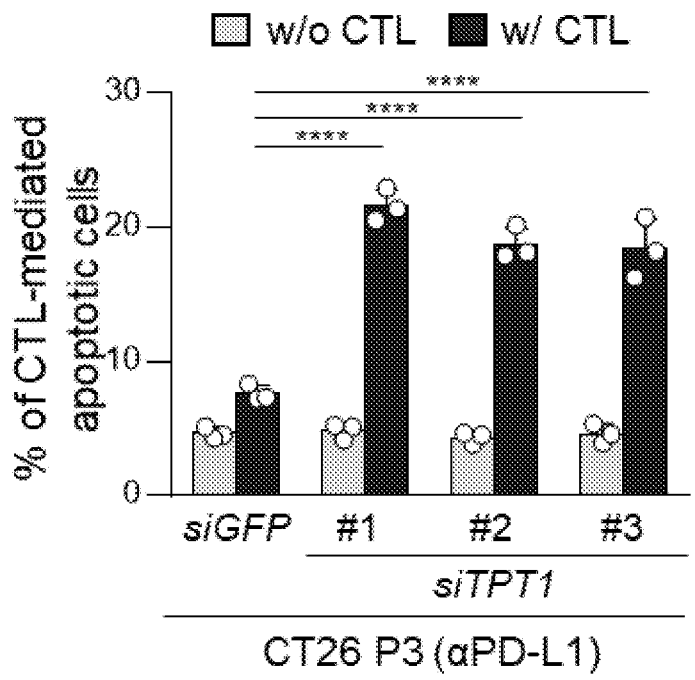

TPT1 knockdown also increased the sensitivity of CT26 P3 cells to apoptosis induced by AH-1-specific CTLs (FIG. 2E).

Figure 2F:
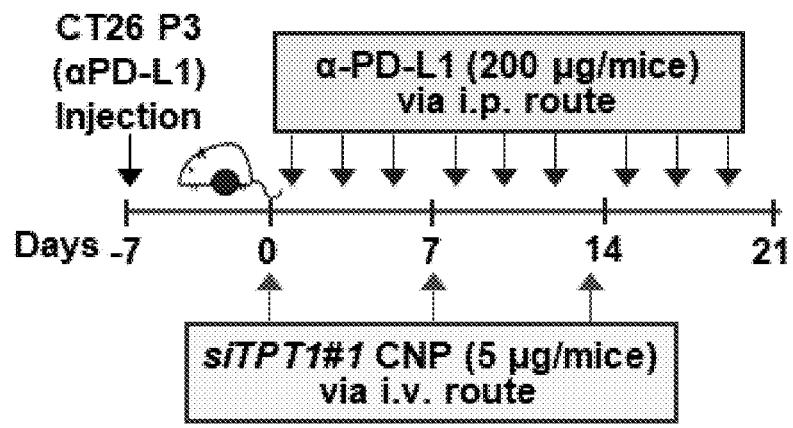

On the basis of the in vitro observations, the present inventors reasoned that in vivo silencing of TPT1 could reverse the refractory phenotypes of CT26 P3 tumors to anti-PD-L1 therapy. To test this, the present inventors treated CT26 P3-bearing mice with anti-PD-L1 therapy along with intravenously-administered chitosan nanoparticles (CNPs) carrying siTPT1 or siGFP for the in vivo delivery of siRNAs to tumors (FIG. 2F).

Figure 2G:
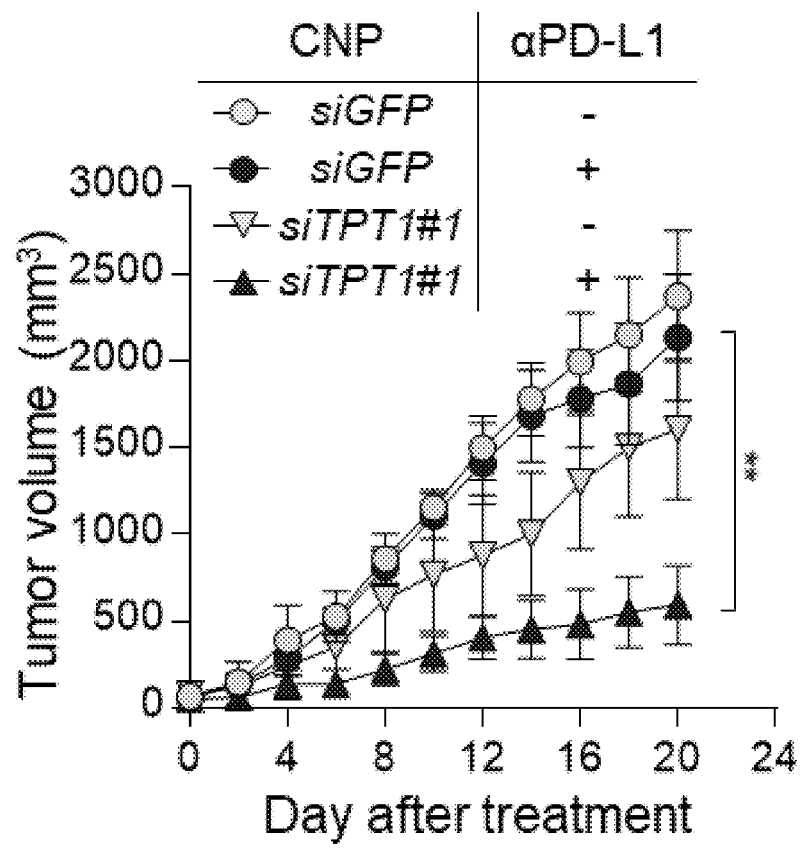
Figure 2H:
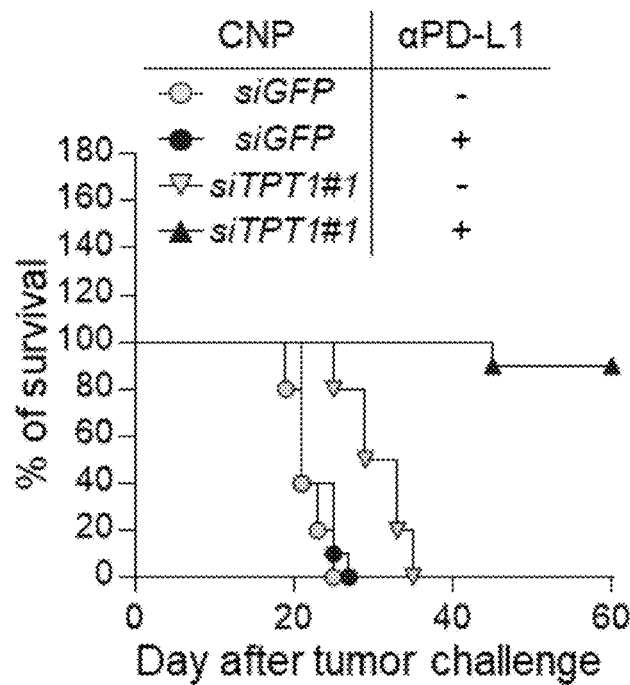
Figure 2I:
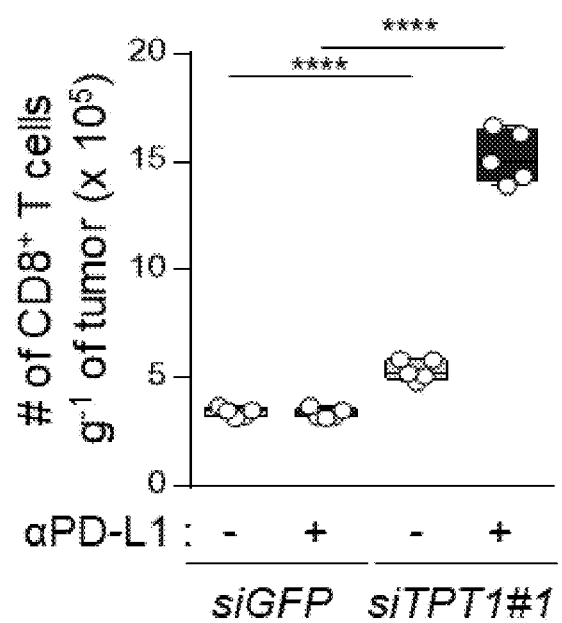
Figure 2J:
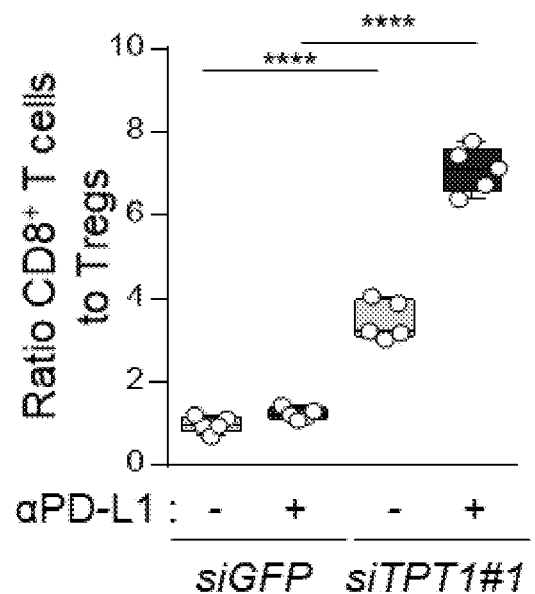
Figure 2K:
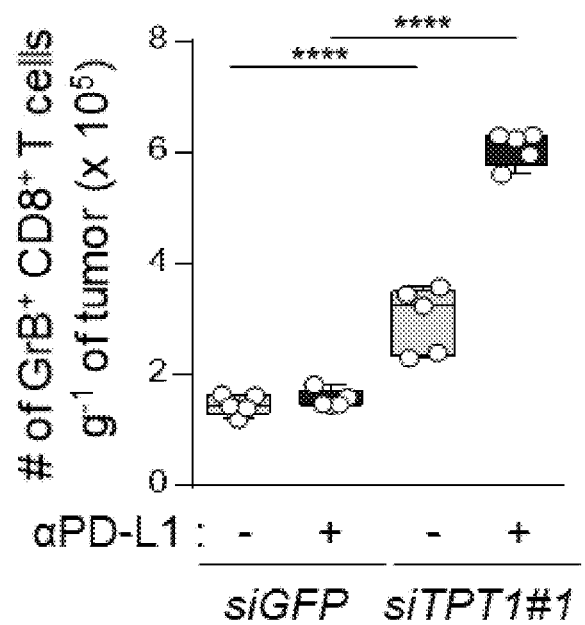
Figure 2L:
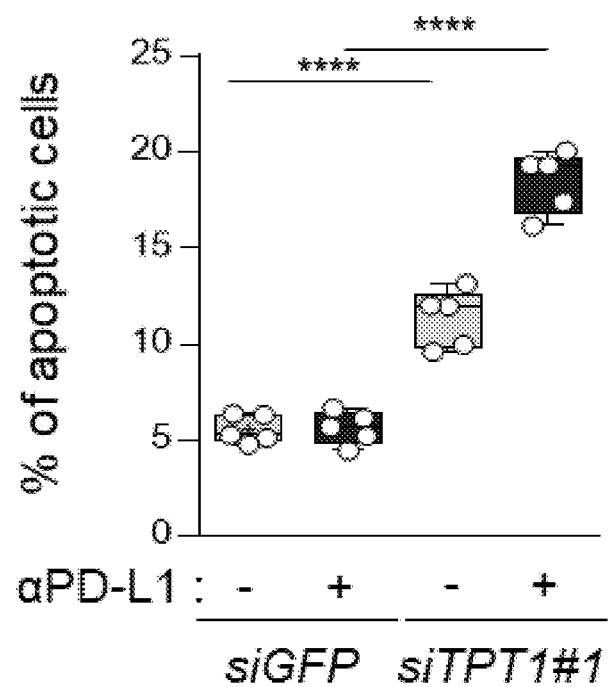

While anti-PD-L1 therapy alone had no effect on tumor growth, the combined therapy with anti-PD-L1 antibody and siTPT1-loaded CNPs profoundly retarded tumor growth (FIG. 2G), and prolonged the survival of the mice (FIG. 2H).

Notably, it was found that the number of functional CD8+ T cells infiltrating the tumor and apoptotic tumor cells was significantly increased in the combined treatment compared to either treatment alone (FIGS. 2I-2L). From the data, it was understood that targeting TCTP could improve the therapeutic efficacy of anti-PD-L1 via reversing immune-refractory tumor phenotypes.

Example 3: Promotion of Immune-Refractory Phenotypes by Ectopic Expression of TCTP, thereby Contributing Resistance to Anti-PD-L1 Therapy Given the crucial role of the TCTP in ICB-refractory tumors, the present inventors examined whether TCTP expression alone could promote the immune-refractory phenotypes. The overexpression of TPT1 in CT26 P0 cells reduced T cell chemotaxis and increased resistance to CTL-mediated apoptosis (FIGS. 3A, 3B, and 3D).

In an effort to elucidate a key molecule in the TCTP-mediated inhibition of T cell chemotaxis, the present inventors noted that chemokines play integral roles in T cell trafficking. Notably, the level of CXCL10 was significantly decreased upon TPT1 overexpression (FIG. 3A), and restoring CXCL10 expression in TCTP-ectopically-expression CT26 P0 cells (FIG. 3B) and CT26 TCTP cells (FIG. 3C) reversed T cell chemotaxis, indicating an important role of CXCL10 in the property mediated by TCTP.

Figure 3A:
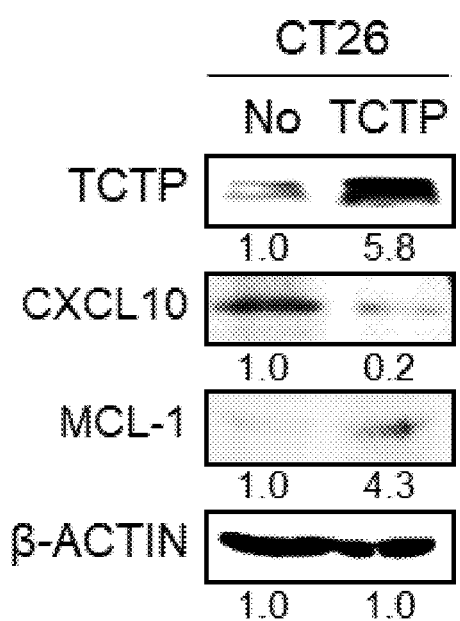
FIGS. 3A, 3B, 3C, 3D, 3E, 3F, 3G, 3H, 3I, 3J, 3K and 3L are views showing effects of the overexpression of TCTP on change in properties of tumor cells. CT26 cells were stably transfected with empty vector (No) or TCTP.
Figure 3B:
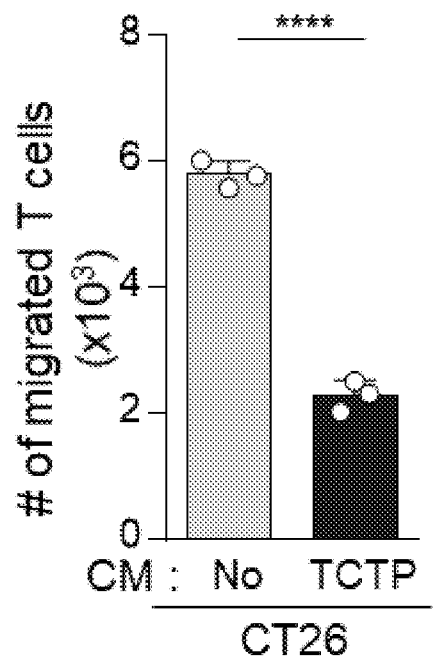
Figure 3C:
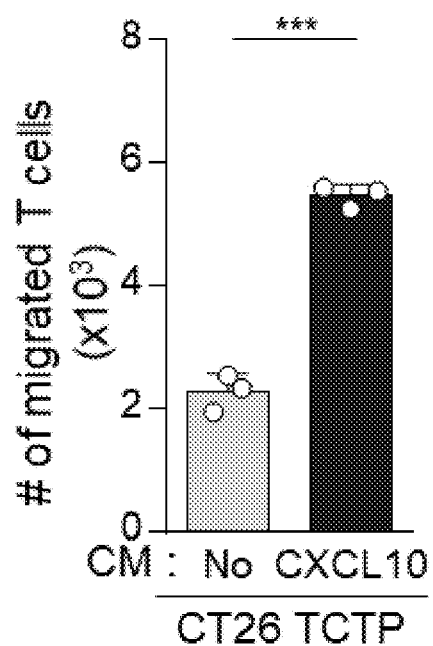
Figure 3D:
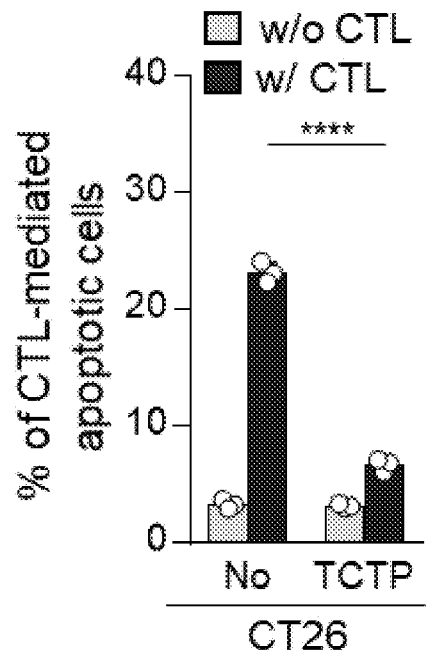
Figure 3E:
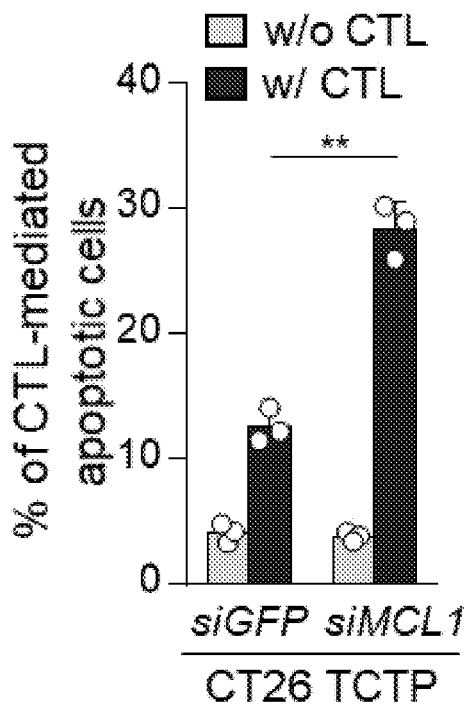

For the TCTP-mediated anti-apoptotic response to CTLs, the present inventors noted an increase in anti-apoptotic protein MCL-1 in CT26 TCTP cells, relative to CT26-no cells (FIG. 3A). The knockdown of MCL-1 restored the susceptibility of CT26 TCTP cells to CTL-mediated apoptosis (FIGS. 3D and 3E).

Figure 3F:
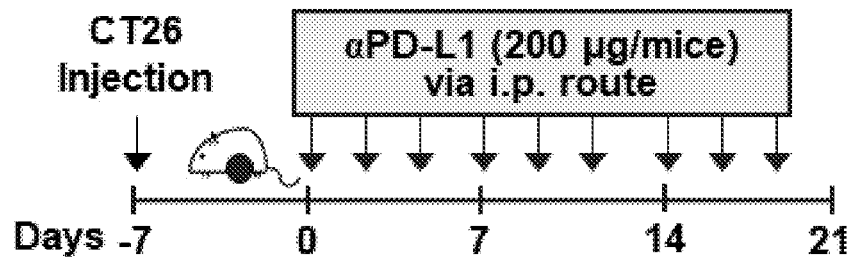
Figure 3G:
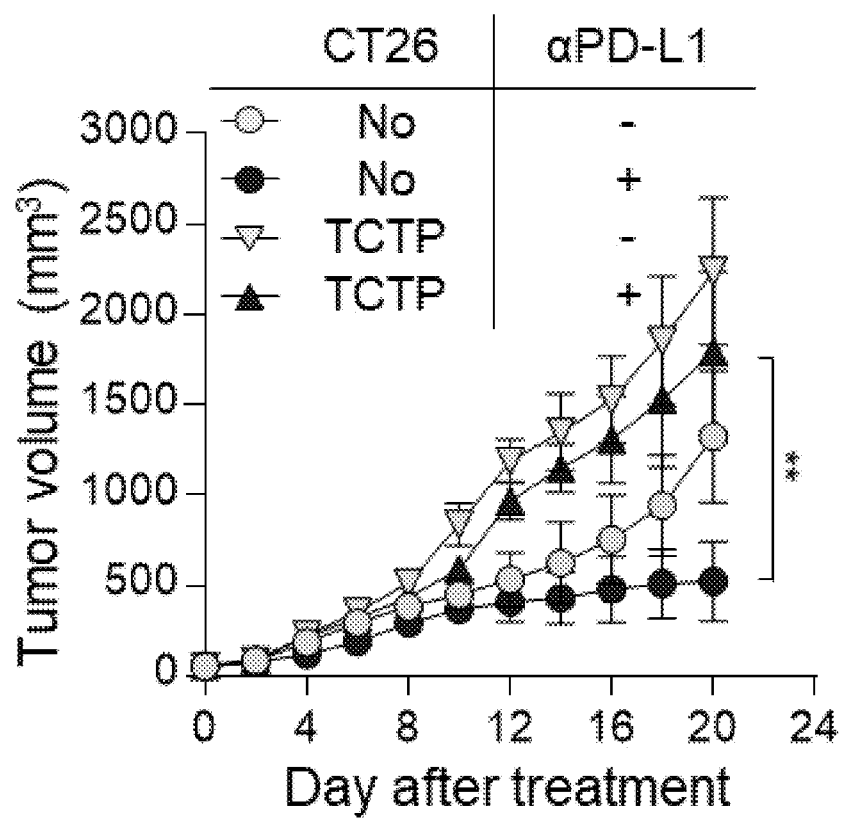
Figure 3H:
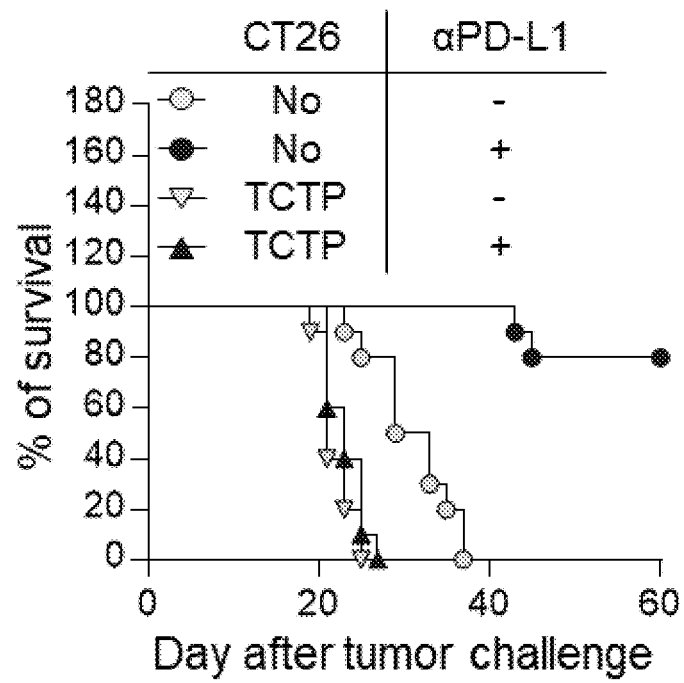
Figure 3I:
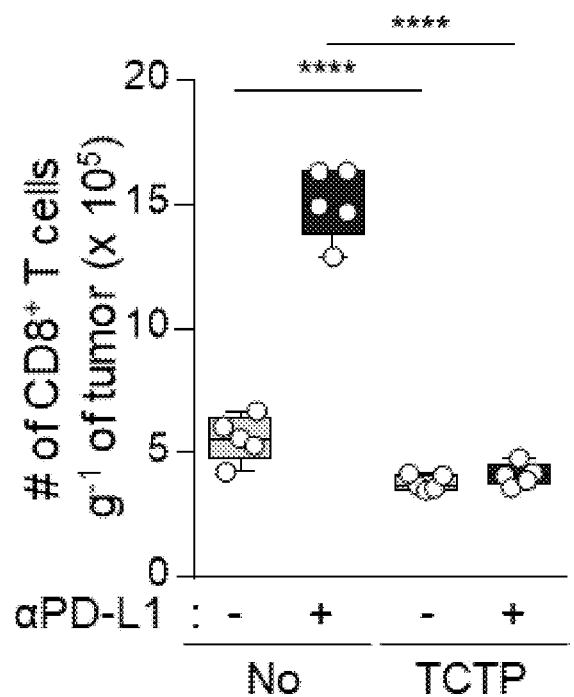
Figure 3J:
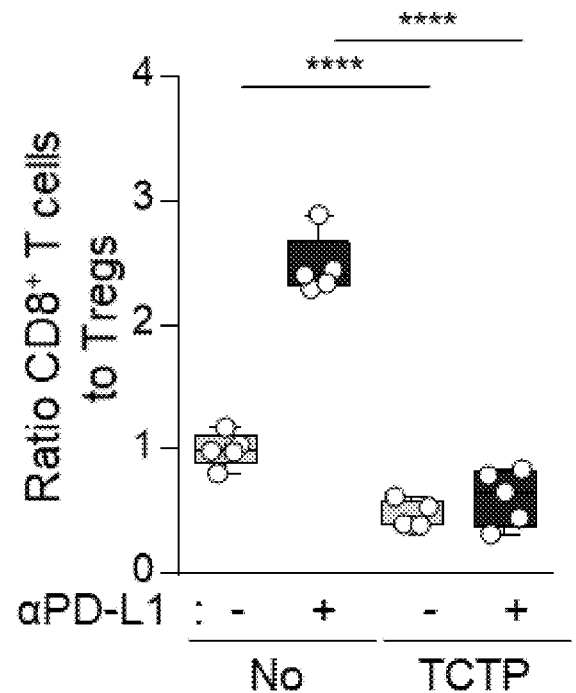
Figure 3K:
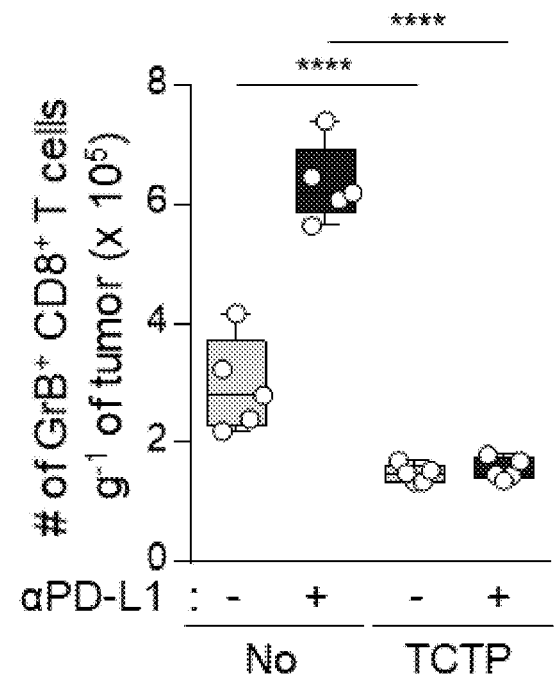
Figure 3L:
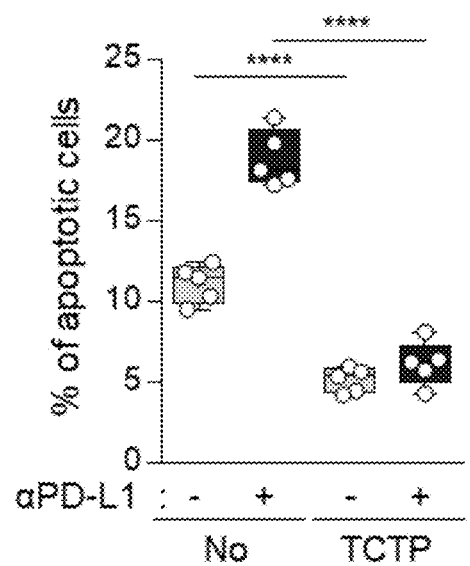

Thus, the present inventors concluded that CXCL10 and MCL-1 were key mediators of the TCTP-induced immune-refractory phenotypes. Consistent with the in vitro results, TCTP overexpression conferred a poor response to anti-PD-L1 therapy in vivo (FIGS. 3F-3H). This was accompanied by decreased numbers of tumor-infiltrated CD8+ T cells, and the ratio of CD8+ T cells to T regs and tumor-reactive CD8+ T cells (FIGS. 3I-3K), as well as the apoptotic cell death of tumor cell populations (FIG. 3L).

Given these results, the present inventors concluded that TCTP itself was sufficient to promote the non-T cell inflamed immune-phenotype and resistance of tumor cells to CTL killing, thereby contributing to anti-PD-L1 therapy resistance.

Figure 4A:
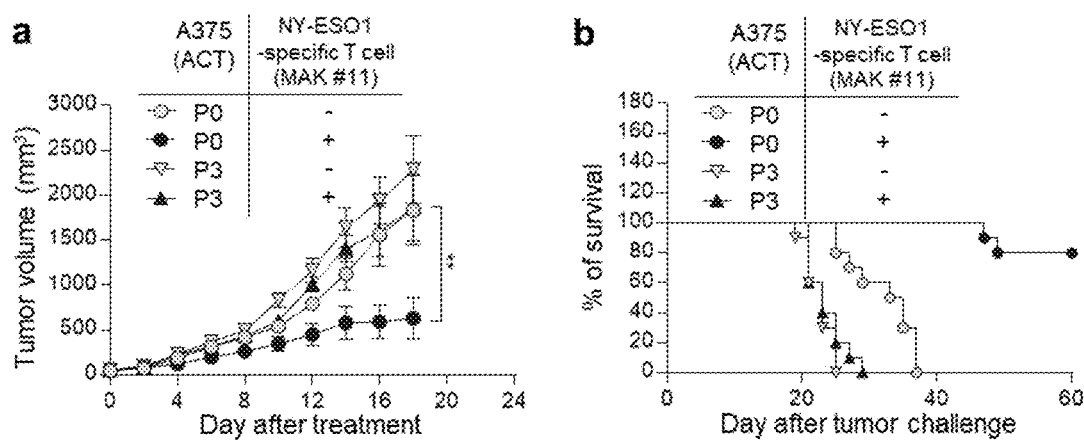
FIG. 4A is a view illustrating the establishment of A375 (NY-ESO1 tumor antigen expression) P3 cell line resistant to human-derived NY-ESO1-specific T cell therapy.

Example 4: Enrichment of TCTP$^+$ Immune-Refractory Cancer Cells by CTL-Mediated Immune Selection As tumor antigen-specific CTLs are key effectors in anti-PD-L1 therapy, the present inventors reasoned that increased TCTP expression under anti-PD-L1 therapy is due to immune selection imposed by CTLs. To test this possibility, the present inventors chose the A375 human melanoma cells, the most typical cancer for the clinical application of adoptive CD8+ T cell transfer therapy (ACT), and established an ACT-refractory A375 P3 model from parental A375 P0 cells by selection with NY-ESO1-specific CD8+ T cells in vivo (FIG. 4A).

Figure 4B:
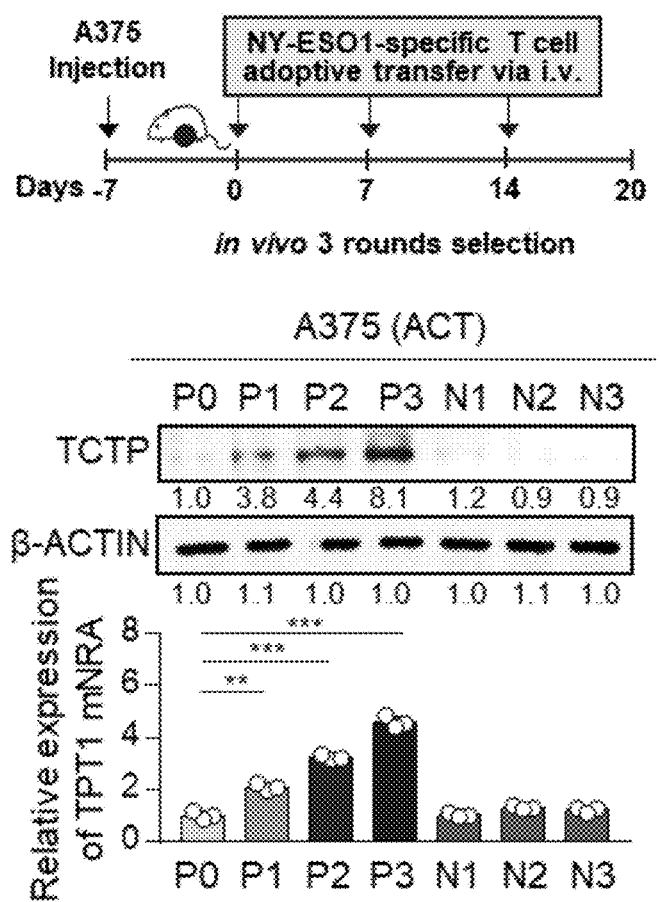
FIGS. 4B, 4C, 4D, 4E, 4F, 4G, 4H, 4I, 4J, 4K, 4L, and 4M illustrate that CTL-mediated immune selection enriches TCTP+ immune-refractory tumor cells.

While the adoptive transfer of NY-ESO1-specific CTLs significantly retarded tumor growth and prolonged mouse survival in A375 P0 tumor-bearing NOD/SCID mice, there was no remarkable therapeutic effects in the A375 P3 tumor-bearing mice. Relevant to the ICB-refractory tumor model, A375 P3 cells had immune-refractory properties, including a lower capacity to induce T cell migration and resistance to CTL-mediated killing. Indeed, the levels of TCTP mRNA and protein were increased in different rounds of CTL-mediated immune selection (FIG. 4B)

Figure 4C:
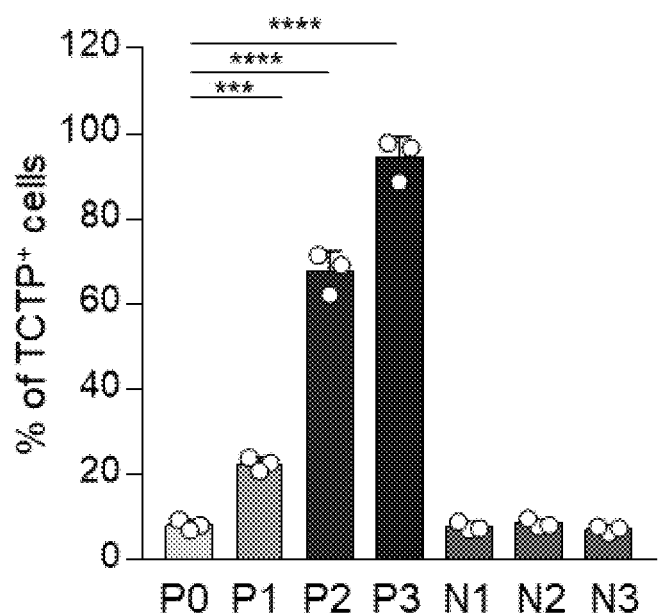

The CTL-mediated immune selection was likely due to the enrichment of TCTP+ cells during the ACT, as evidenced by an increased proportion of TCTP+ cells from around 8.9% in the A375 P0 cells to around 94.9% in the A375 P3 cells (FIG. 4C).

Figure 4D:
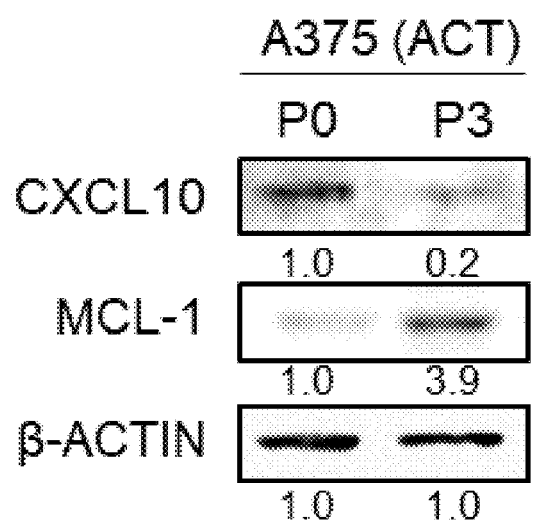

Changes in MCL-1 and CXCL10 protein levels were also observed in the A375 P3 cells compared to the P0 cells (FIG. 4D).

Figure 4E:
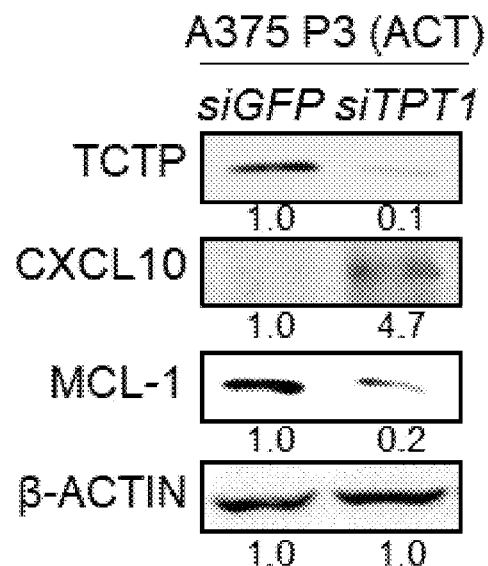
Figure 4F:
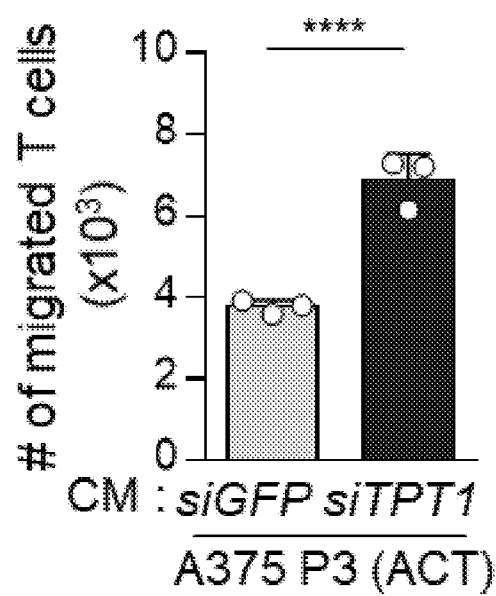
Figure 4G:
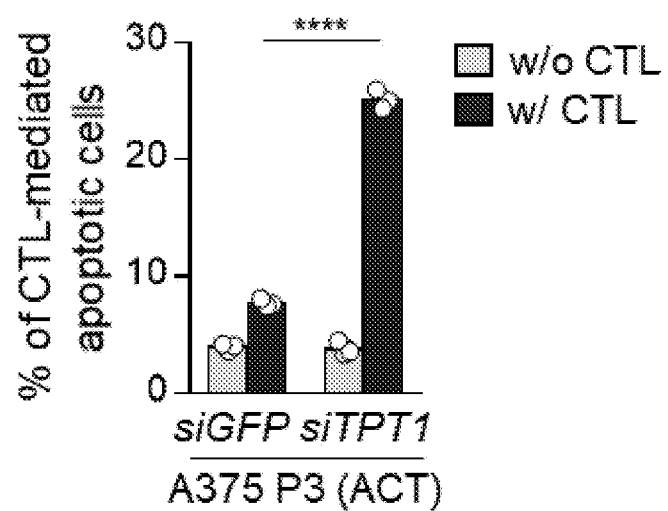

Notably, TCTP knockdown in A375 P3 cells increased T cell migration and sensitized tumor cells to CTL-mediated killing, which was accompanied by profound changes in CXCL10 and MCL-1 (FIGS. 4E-4G).

Figure 4H:
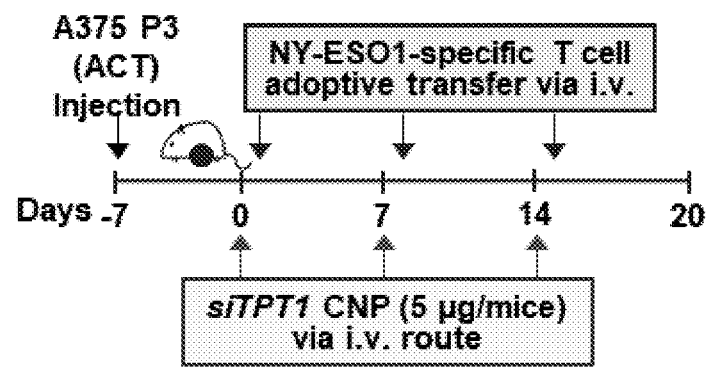
Figure 4I:
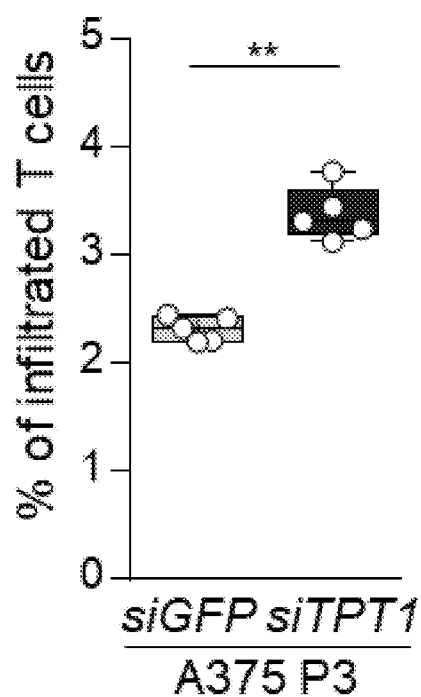
Figure 4J:
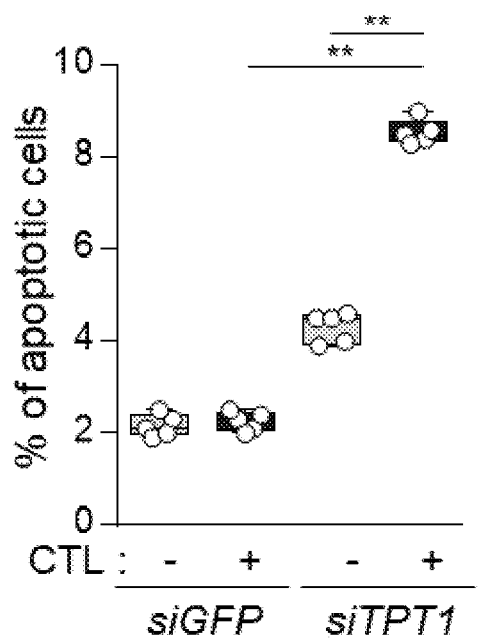

To demonstrate the therapeutic value of inhibiting TCTP, the present inventors inoculated A375 P3 cells into NOD/SCID mice and intravenously administered siTPT1- or siGFP-CNPs (FIG. 4H). The infiltrated functional T cells and apoptotic tumor cells were increased in the siTPT1-treated A375 P3 tumors compared to the siGFP-treated A375 P3 tumors (FIGS. 4I and 4J).

Figure 4K:
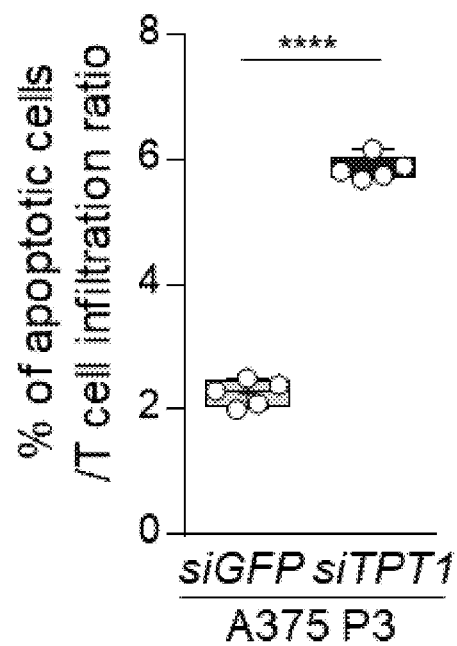
Figure 4L:
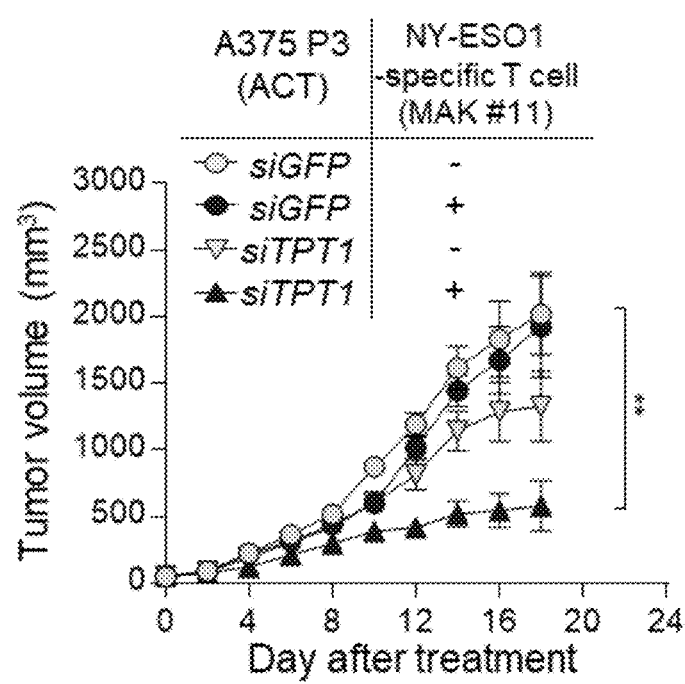
Figure 4M:
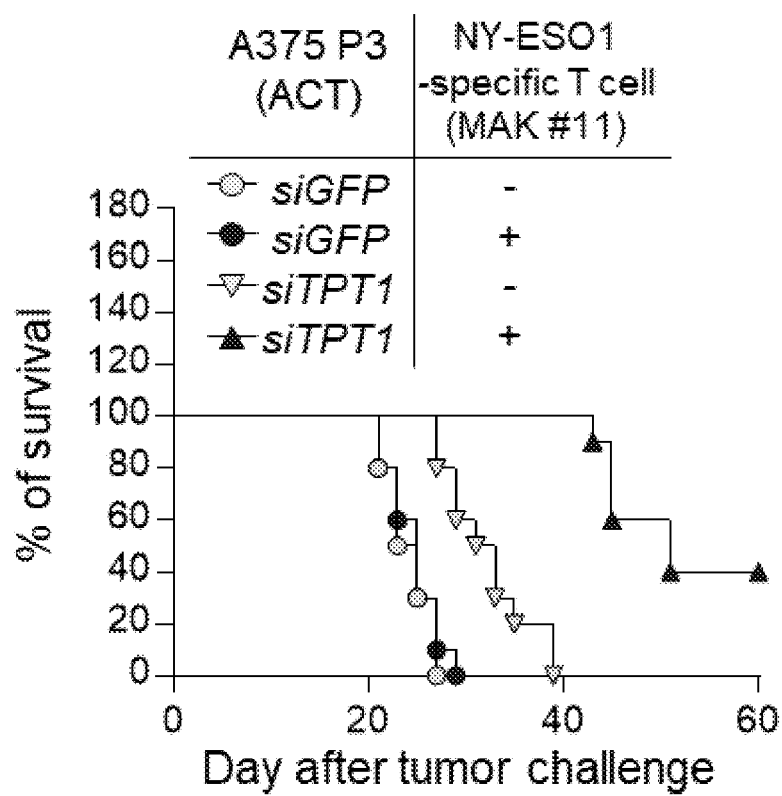

As shown in FIG. 4K, relative to adoptive T cell transfer efficacy, the percentage of apoptotic cells was increased in the tumors of siTPT1-treated mice compared to siGFP-treated mice, indicating that the combined therapeutic effects of targeting TCTP and ACT were affected by both induced CTL-trafficking to the tumor and increased CTL-mediated apoptotic tumor cells. Consistently, combined therapy with siTPT1-CNPs and ACT profoundly retarded tumor growth (FIG. 4L) and prolonged the survival of the mice (FIG. 4M).

Taken together, the data indicate that the enrichment of TCTP+ immune-refractory tumor cells under CTL-mediated immune selection could cause the tumor phenotypes refractory to ACT therapy. Therefore, therapeutic strategies targeting TCTP could reverse immune-refractory phenotypes, thereby improving the efficacy of ACT and ICB therapy.

Figure 5A:
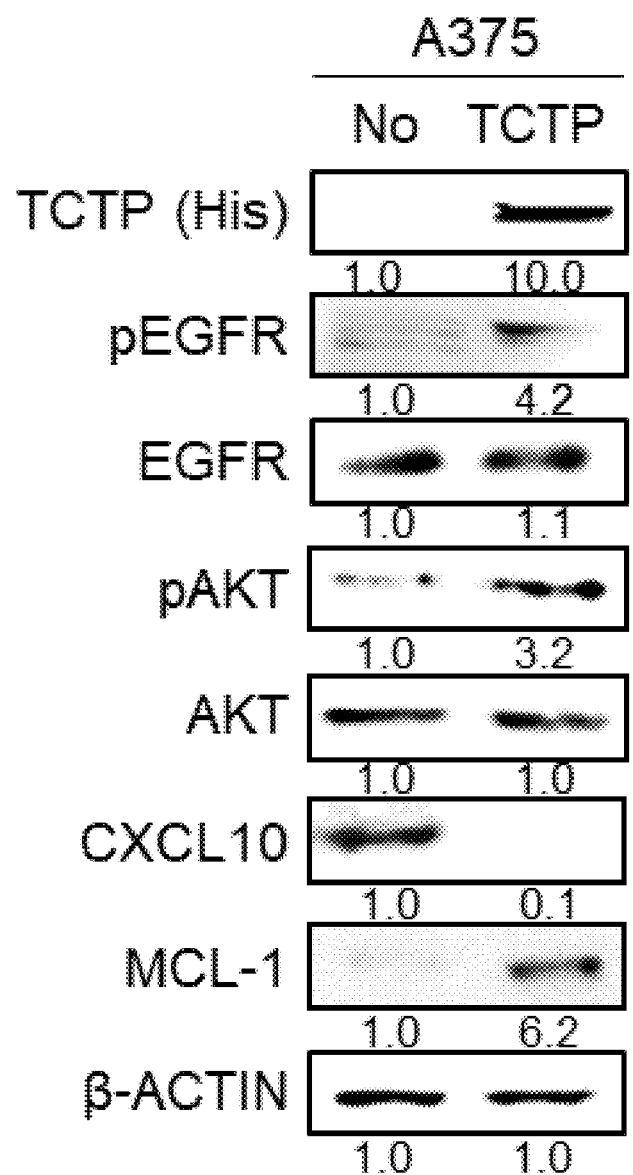
FIGS. 5A, 5B, 5C, 5D, 5E, 5F, 5G and 5H illustrating that TCTP phosphorylation is crucial to activating the EGFR/NANOG signaling pathway via binding with Na, K ATPase.

Example 5: Activation of EGFR-AKT Signaling by TCTP Through Phospho-Dependent Binding with Na, K ATPase, thereby Promoting Immune-Refractory Properties of Tumor Cells The present inventors next attempted to elucidate the signaling pathway by which TCTP conferred the immune-refractory phenotypes. The present inventors found that hyperactivation of the EGFR-AKT pathway was closely linked to the immune escape of tumor cells. In addition, it was revealed that TCTP activates the EGFR signaling pathway via binding to the Na, K ATPase α1 subunit. Notably, TCTP overexpression increased the phosphorylation of both EGFR and AKT, and reduced T cell chemotaxis and CTL susceptibility, which were accompanied by CXCL10 downregulation and MCL-1 upregulation (FIG. 5A).

Figure 5B:
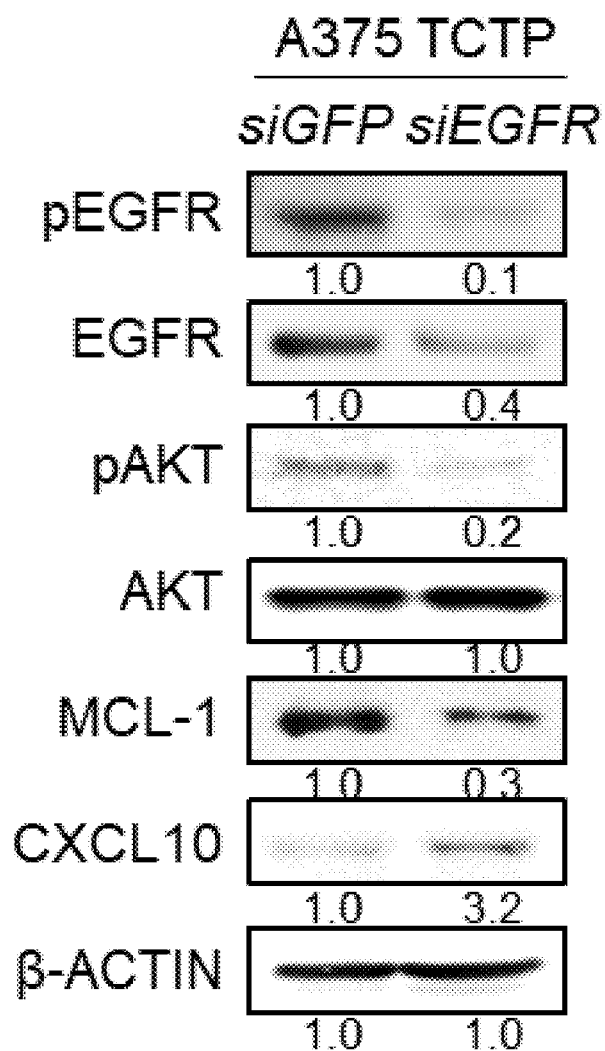

Conversely, the knockdown of EGFR in A375 TCTP cells robustly dampened the levels of phosphorylated AKT and MCL-1, but increased CXCL10 levels (FIG. 5B), demonstrating activation of the EGFR-AKT-MCL-1/CXCL10 axis by TCTP. That is, the overexpression of TCTP promoted the activation of EGFR, AKT, and MCL-1 and inhibited the activation of CXCL10.

Figure 5C:
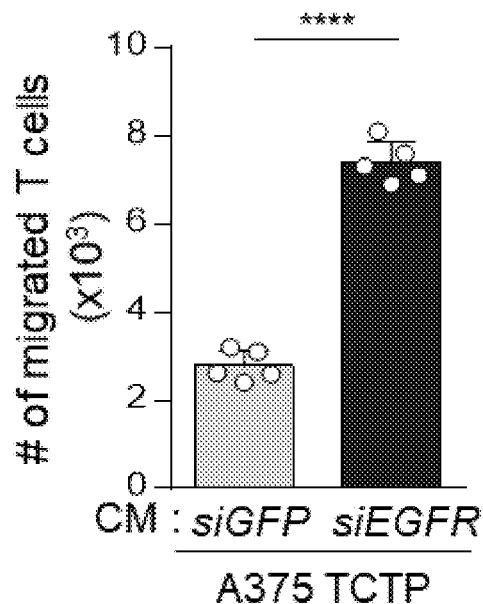
Figure 5D:
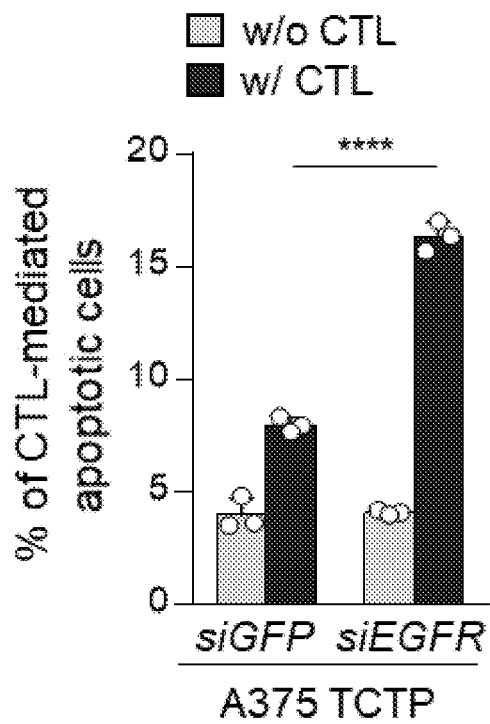

Consistently, loss of EGFR markedly increased T cell chemotaxis and susceptibility to CTLs in A375 TCTP cells (FIGS. 5C and 5D).

Taken together, the present inventors concluded that the hyperactivation of EGFR signaling by TCTP drove the immune-refractory phenotypes By using two mutant forms of TCTP, including a phospho-loss mutant TCTP (TCTP 546A) and a phospho-mimic mutant TCTP (TCTP S46D). it was confirmed that the phosphorylation of TCTP was crucial for EGFR-AKT signaling as well as the immune-refractory properties.

Figure 5E:
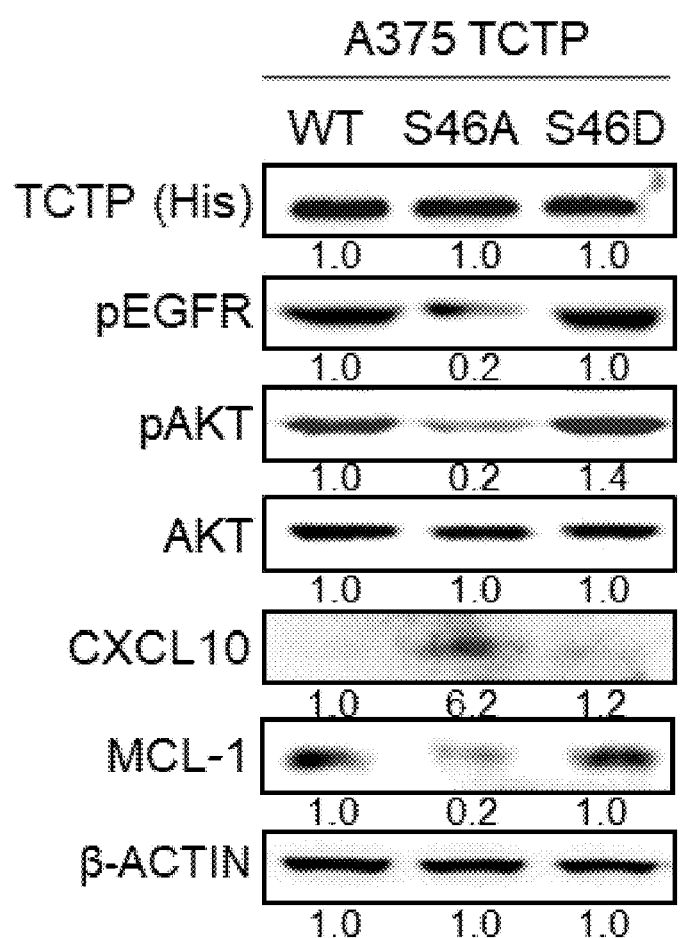
Figure 5F:
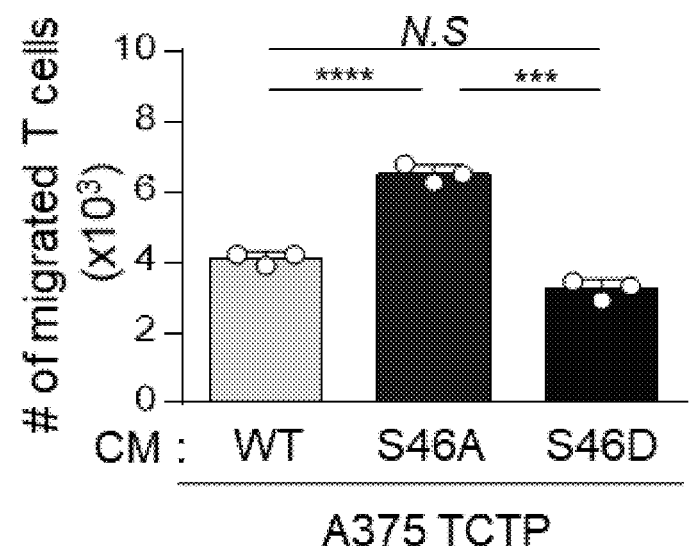
Figure 5G:
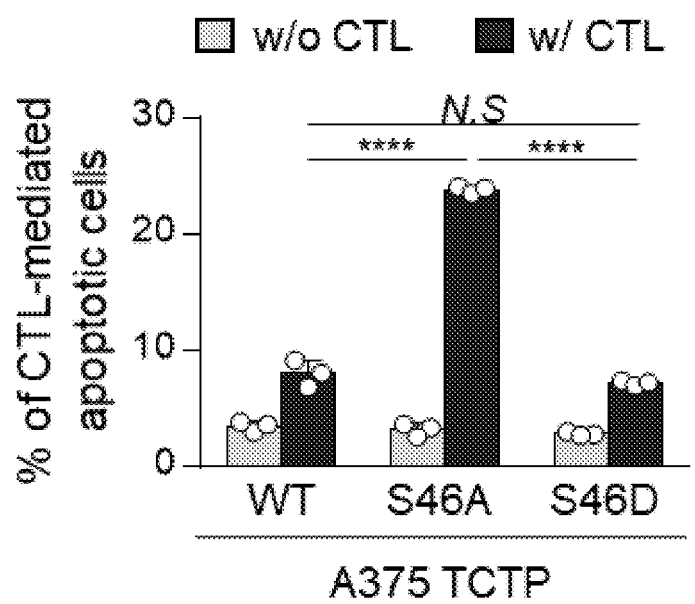

Similar to TCTP WT, TCTP S46D transfection into A375 P0 cells led to the activation of the EGFR-AKT signaling pathway, and promoted the immune-refractory properties of the tumor cells (FIGS. 5E-5G).

In contrast, TCTP S46A failed to reflect the biochemical and functional properties of TCTP WT, demonstrating the important role of phosphorylation in these properties mediated by TCTP (FIGS. 5E-5G).

Figure 5H:
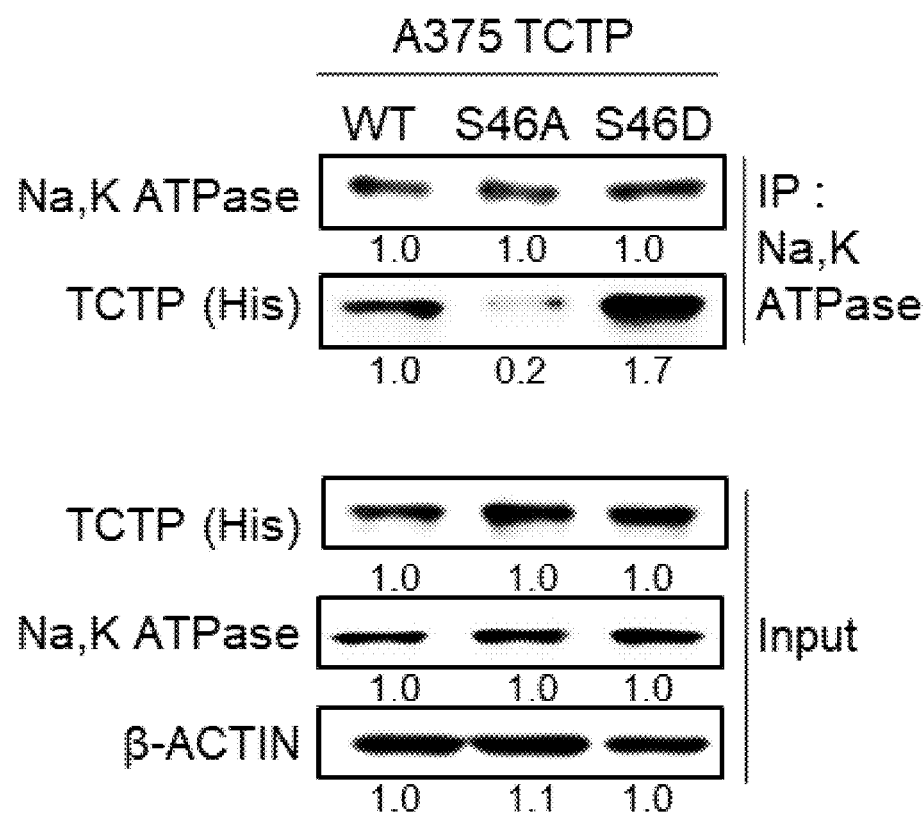

In addition, the binding of TCTP to the Na, K ATPase α1 subunit was found to contribute to the activation of the EGFR signaling pathway. TCTP WT or S46D co-precipitated with Na, K ATPase α1, whereas TCTP S46A did not (FIG. 5H), indicating a phosphorylation-dependent interaction between TCTP and Na, K ATPase α1.

Therefore, it was understood from the data that the phospho-dependent binding of TCTP to Na, K ATPase leads to the activation of EGFR-AKT signaling, indicating that blocking TCTP phosphorylation could be an additional combination strategy with T cell-mediated therapy.

Example 6: Effect of TCTP-Targeting Drug on i) TCTP Inhibition, ii) Sensitization of TCTP$^{high}$ Cancer Cells to T Cell-Mediated Killing, and iii) Increase in T Cell Chemotaxis Capacity of Tumor Cells As a result of having explored that targeting TCTP could be a potential therapeutic strategy to overcome immunotherapy refractoriness, the present inventors aimed to screen clinically-actionable drugs that could target TCTP to reverse the immune-refractory phenotypes of TCTP$^{high}$ tumor cells. It has been suggested that a number of drugs such as dihydroartemisinin (DHA), rapamycin, sertraline, and thioridazine had an inhibitory effect on TCTP function. Indeed, while CT26 TCTP cells were refractory to cisplatin as reported previously, these cells were more susceptible to TCTP-targeting agents, especially to DHA, a clinically-available drug to treat malaria (CT26 No IC$_{50}$=407.6 µM, CT26 TCTP IC$_{50}$=22.67 µM, about 20-fold) (FIG. 6A).

To further investigate the effect of each drug on sensitizing TCTP$^{high}$ tumor cells to CTL-mediated killing, CT26 TCTP tumor cells were incubated with CTLs at various tumor cell-T cell ratios after treatment with a sublethal dose of each drug. Compared to PBS or cisplatin, TCTP-targeting drugs (DHA, rapamycin, sertraline, and thioridazine) augmented CTL-mediated cytotoxicity in a synergistic fashion (FIG. 6B).

To quantify the synergistic effects of treatment of each drug with CTLs, a combination score was calculated based on changes in the percentage of apoptosis in drug-treated tumor cells with or without CTLs (see the following formula 1).

Combination score=(% of active-caspase 3+tumor cells by drug and CTLs)/(% of active-caspase 3+tumor cells by drug).   Formula 1

From this analysis, the present inventors found that the score of the combination with DHA was remarkably higher than other drugs at all ratios (FIG. 6C).

Given these data, the present inventors concluded that DHA was the most effective drug to reverse the immune-refractory phenotypes of TCTP$^{high}$ tumor cells.

To verify the phenotypic effects of DHA in multiple types of TCTP$^{high}$ tumor cells, the present inventors further employed previously established ACT-refractory MDA-MB-231 P3 cells and human cancer cells 526Mel and HCT116 which expressed TCTP at high level. Consistently, the knockdown of TCTP robustly dampened the EGFR-AKT-MCL-1/CXCL10 pathway across all tested cells (FIG. 6D). Notably, DHA treatment resulted in the identical effects on the level of these molecules compared to treatment with siTPT1 (FIG. 6D). Importantly, both siTPT1- and DHA-treated tumor cells were more susceptible to CTL-mediated apoptosis, and they also had increased T cell chemotaxis capacity compared to siGFP- or PBS-treated control cells, respectively (FIGS. 6, E and F).

These results demonstrated that the biochemical and functional properties of the TCTP axis were conserved across multiple types of cancer cells and that impeding TCTP signaling with DHA is a widely applicable strategy for controlling immune-refractory TCTP$^{high}$ cancer cells.

Example 7: Targeting TCTP by Using DHA Reverses Resistance to i) ACT Therapy and ii) Anti-PD-L1 Therapy in Preclinical Mode Given the observations in vitro, the present inventors reasoned that the in vivo administration of DHA should reverse resistance of TCTP$^{high}$ tumor cells to T cell-mediated therapy.

To test this possibility, ACT-refractory A375 P3 tumor-bearing NOD/SCID mice were treated cognate NY-ESO1-specific CTLs with or without DHA (FIG. 7A). While CTLs alone had no effect on tumor growth, dual therapy with CTLs and DHA retarded tumor growth (FIG. 7B), and prolonged survival of the mice compared to the other groups (FIG. 7C).

The proportion of NY-ESO1-specific CTLs in the tumors was increased in the tumors of DHA-treated mice compared to those in PBS-treated mice (FIG. 7D), and the overall cytotoxic effects of these CTLs were greater after treatment with DHA relative to the PBS control, as indicated by the percentage of apoptotic cells in the tumor populations (FIGS. 7E and 7F).

Next, the present inventors expanded the preclinical therapeutic value of DHA in ICB therapy. To do this, ICB-refractory CT26 P3 tumor-bearing mice were administered anti-PD-L1 antibody alone or combined with DHA (FIG. 7G).

Compared to treatment with anti-PD-L1 or DHA alone, combined therapy with anti-PD-L1 and DHA showed a remarkable therapeutic effect in CT26 P3 tumor-bearing mice (FIG. 7H).

Importantly, while 90% of the mice that received both the anti-PD-L1 blockade agent and DHA survived, all of the mice in the other groups died (FIG. 7I).

In addition, the numbers of infiltrated functional CD8+ T cells and the cytotoxic effect of these CTLs were significantly higher in the co-treated mice group than in the other mice groups (FIGS. 7J-7M).

Taken together, it was concluded that targeting TCTP by using the actionable drug, DHA, is potential combinational strategy enhancing the response to ACT as well as ICB therapy.

In addition, the present inventors reasoned that a TCTP neutralizing antibody targeting TCTP as well as DHA could reverse anticancer immune resistance.

First, to examine whether extracellular secretion of TCTP also increases in ACT-refractory A375 P3, TCTP protein levels in intracellular and extracellular supernatants of A375 P0 and A375 P3 were analyzed. As a result, the extracellular secretion of TCTP was found to also increase in A375 P3 resistant cancer (FIG. 8A).

Furthermore, in order to examine the effect of an anti-TCTP neutralizing antibody targeting TCTP on anticancer immune resistance, investigation was made of the effect of treatment with CTL and anti-TCTP neutralizing antibody on apoptosis percentage of tumor cells and the TCTP-AKT-MCL-1, NANOG pathway. As a result, when a TCTP neutralizing antibody was used to target TCTP, it was found that phenotypes to anticancer immune resistance was decreased (FIG. 8B) and the previously reported immune resistance and the expression of the cross resistance (cisplatin resistance) and multiple malignance (cancer metastasis and cancer stemness) regulator NANOG as well as the AKT signaling pathway were reduced (FIG. 8c).

From the result, it was understood that the TCTP secreted outside tumor cells play a crucial role in the therapeutic resistance and multiple malignancy phenotypes of resistant cancer and the neutralization of TCTP through anti-TCTP neutralizing antibody could reverse the phenotypes of resistant cancer.

In addition, the present inventors revealed in samples of patients with various carcinomas that there is a significant correlation between immune resistance and the expression of NANOG, a factor regulating cross resistance (cisplatin resistance) and multiple malignancy (cancer metastasis and cancer stemness) depending on the expression level ($TCTP^{high}/TCTP^{low}$) of TCTP.

The present inventors also found that in TC-1 LP3 constructed as an immune checkpoint antibody therapy-refractory orthostatic lung cancer model, intracellular and extracellular TCTP secretion remarkably increases (FIG. 10) and when TCTP was neutralized through an anti-TCTP neutralizing antibody, the previously reported immune resistance and cross resistance (cisplatin resistance) was decreased and multiple malignancy (cancer metastasis and cancer stemness) was also reduced.

What is claimed is:

1. A method for treating cancer comprising:
   (a) measuring presence or expression of TCTP (translationally controlled tumor protein) at a protein or gene level in a sample isolated from an individual suffering from the cancer;
   (b) identifying the individual whose sample having a higher presence or expression level of the TCTP protein or gene measured in step (a) compared to the presence or expression level of the TCTP protein or gene measured in a reference sample; and
   (c) administering a pharmaceutical composition comprising an immunotherapeutic agent and a TCTP inhibitor as an active ingredient to the individual identified in step (b).

2. The method of claim 1, wherein the immunotherapeutic agent is an immune checkpoint blocker or an adoptive cell therapeutic agent.

3. The method of claim 1, wherein the TCTP inhibitor is an antibody or an antigen-binding fragment thereof, an antibody-drug conjugate, a compound, a peptide, a fusion protein, or an aptamer, which all bind specifically to TCTP; or an siRNA, an shRNA, a miRNA, a ribozyme, or an antisense oligonucleotide, which all bind complementarily to a TCTP gene.

4. The method of claim 1, wherein the TCTP inhibitor is one selected from the group consisting of dihydroartemisinin (DHA), rapamycin, sertraline, and thioridazine.

5. The method of claim 1, wherein the cancer is selected from non-small cell lung cancer, small cell lung cancer, liver cancer, bone cancer, tongue cancer, laryngeal cancer, renal cell cancer, colorectal cancer, ovarian cancer, breast cancer, pancreatic cancer, gastric carcinoma, bladder cancer, esophageal cancer, mesothelioma, melanoma, head and neck cancer, thyroid cancer, sarcoma, prostate cancer, glioblastoma, cervical cancer, thymic carcinoma, leukemia, lymphomas, myelomas, Merkle cell cancer, and hematologic malignancies.

* * * * *